US012060599B2

(12) United States Patent
Apte et al.

(10) Patent No.: US 12,060,599 B2
(45) Date of Patent: Aug. 13, 2024

(54) METHOD AND SYSTEM FOR MICROBIOME-DERIVED DIAGNOSTICS AND THERAPEUTICS FOR BACTERIAL VAGINOSIS

(71) Applicant: PSOMAGEN, INC., Rockville, MD (US)

(72) Inventors: Zachary Apte, San Francisco, CA (US); Jessica Richman, San Francisco, CA (US); Daniel Almonacid, San Francisco, CA (US); Siavosh Rezvan Behbahani, San Francisco, CA (US)

(73) Assignee: Psomagen, Inc., Rockville, MD (US)

( * ) Notice: Subject to any disclaimer, the term of this patent is extended or adjusted under 35 U.S.C. 154(b) by 1495 days.

(21) Appl. No.: 16/084,945

(22) PCT Filed: Sep. 9, 2016

(86) PCT No.: PCT/US2016/051156
§ 371 (c)(1),
(2) Date: Sep. 13, 2018

(87) PCT Pub. No.: WO2017/044886
PCT Pub. Date: Mar. 16, 2017

(65) Prior Publication Data
US 2019/0367968 A1 Dec. 5, 2019

Related U.S. Application Data

(60) Provisional application No. 62/216,082, filed on Sep. 9, 2015.

(51) Int. Cl.
*C12Q 1/04* (2006.01)
*A61K 35/747* (2015.01)
(Continued)

(52) U.S. Cl.
CPC .............. *C12Q 1/04* (2013.01); *A61K 35/747* (2013.01); *C12Q 1/689* (2013.01); *G16B 5/00* (2019.02);
(Continued)

(58) Field of Classification Search
CPC ........ C12Q 1/689; G16B 30/10; G16B 40/20; G16B 30/00; G16H 50/20; G16H 50/50; G01N 2800/36
See application file for complete search history.

(56) References Cited

U.S. PATENT DOCUMENTS

| 4,683,202 A | 7/1987 | Mullis |
| 2009/0127589 A1 | 5/2009 | Rothberg et al. |

(Continued)

FOREIGN PATENT DOCUMENTS

| WO | 2014165810 A1 | 10/2014 |
| WO | 2015022297 A2 | 2/2015 |

OTHER PUBLICATIONS

Macklaim et al. comparative meta-RNA-seq of the vaginal microbiota and differential expression by Lactobacillus iners in health and dysbiosis Microbiome vol. 1, article 12 (Year: 2013).*

(Continued)

*Primary Examiner* — Russell S Negin
*Assistant Examiner* — Guozhen Liu
(74) *Attorney, Agent, or Firm* — Morgan, Lewis & Bockius LLP

(57) ABSTRACT

Methods, compositions, and systems are provided for detecting one or more a bacterial vaginosis issues by characterizing the microbiome of an individual, monitoring such effects, and/or determining, displaying, or promoting a therapy for the bacterial vaginosis issue. Methods, compositions, and systems are also provided for generating and comparing microbiome composition and/or functional (Continued)

diversity datasets. Methods, compositions, and systems are also provided for generating a characterization model and/or therapy model for bacterial vaginosis.

6 Claims, 12 Drawing Sheets

(51) Int. Cl.

| | |
|---|---|
| C12Q 1/689 | (2018.01) |
| G16B 5/00 | (2019.01) |
| G16B 20/00 | (2019.01) |
| G16B 25/10 | (2019.01) |
| G16B 30/10 | (2019.01) |
| G16B 40/20 | (2019.01) |
| G16B 40/30 | (2019.01) |
| G16B 50/10 | (2019.01) |
| G16H 10/40 | (2018.01) |
| G16H 50/20 | (2018.01) |
| G16H 50/50 | (2018.01) |
| G16B 30/00 | (2019.01) |
| G16H 50/70 | (2018.01) |

(52) U.S. Cl.
CPC ............. *G16B 20/00* (2019.02); *G16B 25/10* (2019.02); *G16B 30/10* (2019.02); *G16B 40/20* (2019.02); *G16B 40/30* (2019.02); *G16B 50/10* (2019.02); *G16H 10/40* (2018.01); *G16H 50/20* (2018.01); *G16H 50/50* (2018.01); *C12Q 2600/106* (2013.01); *C12Q 2600/158* (2013.01)

(56) References Cited

U.S. PATENT DOCUMENTS

| | | | |
|---|---|---|---|
| 2010/0035252 A1 | 2/2010 | Rothberg et al. | |
| 2013/0121968 A1 | 5/2013 | Quay | |
| 2013/0288988 A1* | 10/2013 | Cartwright | C12Q 1/689 514/24 |
| 2015/0044687 A1 | 2/2015 | Schmitt et al. | |
| 2015/0211055 A1 | 7/2015 | Apte et al. | |
| 2015/0211078 A1 | 7/2015 | Apte et al. | |
| 2015/0213193 A1 | 7/2015 | Apte et al. | |
| 2016/0110515 A1* | 4/2016 | Apte | G16H 50/20 506/7 |
| 2017/0166955 A1* | 6/2017 | Birnboim | C12Q 1/6806 |

OTHER PUBLICATIONS

Fettweis et al. Species-level classification of the vaginal microbiome BMC Genomics vol. 13 article S17 (Year: 2012).*
Hay, Phillip. "Recurrent bacterial vaginosis." Current Opinion in infectious diseases 22.1 (2009): 82-86. (Year: 2009).*
Aagaard, Kjersti, et al. "The placenta harbors a unique microbiome." Science translational medicine 6.237 (2014): 237ra65-237ra65. (Year: 2014).*
Obata-Yasuoka, Mana, et al. "A multiplex polymerase chain reaction-based diagnostic method for bacterial vaginosis." Obstetrics & Gynecology 100.4 (2002): 759-764. (Year: 2002).*
Ling, Zongxin, et al. "Molecular analysis of the diversity of vaginal microbiota associated with bacterial vaginosis." BMC genomics 11 (2010): 1-16. (Year: 2010).*
Fettweis, Jennifer M., et al. "Species-level classification of the vaginal microbiome." BMC genomics 13.8 (2012): 1-9. (Year: 2012).*
Castro-Nallar, Eduardo, et al. "Composition, taxonomy and functional diversity of the oropharynx microbiome in individuals with schizophrenia and controls." PeerJ 3 (2015): e1140. (Year: 2015).*

Altschul et al., "Basic Local Alignment Search Tool", J Mol Biol., vol. 215, 1990, pp. 403-410.
Altschul et al., "Gapped BLAST and PSI-BLAST: A New Generation of Protein Database Search Programs", Nucleic Acids Research, vol. 25, No. 17, 1997, pp. 3389-3402.
Arnheim et al., "Polymerase Chain Reaction", Chem. Eng. News, vol. 68, No. 40, 1990, pp. 36-47.
Ausubel et al., "Current Protocols in Molecular Biology", vol. 1, 1994, 18 pages.
Barringer et al., "Blunt-end and Single-strand Ligations by *Escherichia coli* Ligase: Influence on an In Vitro Amplication Scheme", Gene, vol. 89, No. 1, Apr. 30, 1990, pp. 117-122.
Clarke et al., "Continuous Base Identification for Single-Molecule Nanopore DNA Sequencing", Nature Nanotechnology, vol. 4, Apr. 2009, pp. 265-270.
Guatelli et al., "Isothermal, In Vitro Amplification of Nucleic Acids by a Multienzyme Reaction Modeled after Retroviral Replication", Proc. Natl. Acad. Sci. USA, vol. 87, Mar. 1990, pp. 1874-1878.
Harlow et al., "Antibodies: A Laboratory Manual", Cold Spring Harbor Laboratory, 1988, pp. 139-241.
Innis et al., "PCR Protocols: A Guide to Methods and Applications", Academic Press, Inc., 1990, 8 pages.
International Application No. PCT/US2016/051156, International Preliminary Report on Patentability, Mar. 22, 2018, 9 pages.
International Application No. PCT/US2016/051156, Invitation to Pay Additional Fees, Oct. 28, 2016, 2 pages.
International Application No. PCT/US2016/051156, "International Search Report and Written Opinion", Jan. 10, 2017, 12 pages.
Kriegler, "Gene Transfer and Expression: A Laboratory Manual", Stockton Press, 1990, 6 pages.
Kwoh et al., "Transcription-Based Amplification System and Detection of Amplified Human Immunodeficiency Virus Type 1 With a Bead-based Sandwich Hybridization Format", Proc. Natl. Acad. Sci. USA, vol. 86, Feb. 1989, pp. 1173-1177.
Landegren et al., "A Ligase-Mediated Gene Detection Technique", Science, vol. 241, Aug. 26, 1988, pp. 1077-1080.
Lomell et al., "Quantitative Assays based on the use of Replicatable Hybridization Probes", Clinical Chemistry, vol. 35, No. 9, 1989, pp. 1826-1831.
Mahe et al., "Swarm: Robust and Fast Clustering Method for Amplicon-based Studies", PeerJ, vol. 2, e593, Sep. 25, 2014, pp. 1-13.
Mirebrahim et al., "De Novo Meta-Assembly of Ultra-Deep Sequencing Data", Bioinformatics, vol. 31, 2015, pp. i9-i16.
Rognes et al., "VSEARCH: A Versatile Open Source Tool for Metagenomics", PeerJ, vol. 4, e2584, Oct. 18, 2016, pp. 1-22.
Sambrook et al., "Molecular Cloning: A Laboratory Manual", Cold Spring Harbor, vol. 1, 3rd Edition, 2001, 79 pages.
Tatusov et al., "The COG Database: A Tool for Genome-Scale Analysis of Protein Functions and Evolution", Nucleic Acids Research, vol. 28, No. 1, 2000, pp. 33-36.
Van Brunt, "Amplifying Genes: PCR and its Alternatives", Bio/Technology, vol. 8, 1990, pp. 291-294.
Wu et al., "The Ligation Amplification Reaction (LAR)-Amplification of Specific DNA Sequences using Sequential Rounds of Template-Dependent Ligation", Genomics, vol. 4, No. 4, 1989, pp. 560-569.
Mastromarino, "Bacterial vaginosis: a review on clinical trials with probiotics," New Microbiologica, vol. 36, pp. 229-238 (2013).
Schloss, "Introducing DOTUR, a Computer Program for Defining Operational Taxonomic Units and Estimating Species Richness," Applied and Environmental Microbiology, vol. 71, No. 3, pp. 1501-1506 Mar. 2005.
Shafiei, "BioMiCo: a supervised Bayesian model for inference of microbial community structure," Microbiome, pp. 1-15 (2015).
Shipitsyna, "Composition of the Vaginal Microbiota in Women of Reproductive Age—Sensitive and Specific Molecular Diagnosis of Bacterial Vaginosis Is Possible?" PLOS ONE, vol. 8, Issue 4 (2013).
Yeoman, "A Multi-Omic Systems-Based Approach Reveals Metabolic Markers of Bacterial Vaginosis and Insight into the Disease," PLOS ONE, vol. 8, Issue 2 (2013).
Extended European Search Report issued on Apr. 15, 2019 in European Patent Application No. 16845219.1.

(56) References Cited

OTHER PUBLICATIONS

First Office Action issued on Sep. 30, 2020 in Chinese Patent Application No. 201680065082.5 (English translation).
Communication issued Jun. 29, 2023 for counterpart European Patent Application No. 16845219.1.
Kuczynski et al., "Experimental and analytical tools for studying the human microbiome", 2011, Nature Review Genetics, vol. 13, p. 47-58, XP055252622.
Franzosa, et al., "Relating the metatranscriptome and metagenome of the human gut", 2014, Proceedings of the National Academy of Sciences, vol. 111, pg. E2329-E2338, XP055519622.

* cited by examiner

METHOD AND SYSTEM FOR MICROBIOME-DERIVED DIAGNOSTICS AND THERAPEUTICS FOR BACTERIAL VAGINOSIS

CROSS-REFERENCE TO RELATED APPLICATIONS

The present application is a U.S. National Phase of International Application No. PCT/US2016/051156, filed Sep. 9, 2016, which claims benefit of priority to U.S. Provisional Application No. 62/216,082, filed Sep. 9, 2015, the disclosures of which are incorporated by reference herein.

BACKGROUND

A microbiome is an ecological community of commensal, symbiotic, and pathogenic microorganisms that are associated with an organism. The human microbiome comprises more microbial cells than human cells, but characterization of the human microbiome is still in nascent stages due to limitations in sample processing techniques, genetic analysis techniques, and resources for processing large amounts of data. Nonetheless, the microbiome is suspected to play at least a partial role in a number of health/disease-related states (e.g., preparation for childbirth, diabetes, auto-immune disorders, gastrointestinal disorders, rheumatoid disorders, neurological disorders, etc.).

Given the profound implications of the microbiome in affecting a subject's health, efforts related to the characterization of the microbiome, the generation of insights from the characterization, and the generation of therapeutics configured to rectify states of dysbiosis should be pursued. Current methods and systems for analyzing the microbiomes of humans and providing therapeutic measures based on gained insights have, however, left many questions unanswered. In particular, methods for characterizing certain health conditions and therapies (e.g., probiotic therapies) tailored to specific subjects based upon microbiome compositional or functional diversity features have not been viable due to limitations in current technologies.

As such, there is a need in the field of microbiology for a new and useful method and system for characterizing health conditions in an individualized and population-wide manner. This invention creates such a new and useful method and system.

BRIEF SUMMARY

In a first aspect, the present invention provides a method for identification and classification of occurrence of a microbiome associated with bacterial vaginosis or screening for the presence or absence of a microbiome associated with bacterial vaginosis in an individual and/or determining a course of treatment for an individual human having a microbiome composition associated with a health condition derived from bacterial vaginosis, the method comprising:
providing a sample comprising microorganisms from the individual human;
determining an amount(s) of one or more of the following in the sample:
(a) bacteria and/or archaeal taxon or gene sequence corresponding to gene functionality as set forth in Table A;
(b) unicellular eukaryotic taxon or gene sequence corresponding to gene functionality,
comparing the determined amount(s) to a condition pattern or signature having cut-off or probability values for amounts of the microorganisms taxon and/or gene sequence for an individual having a microbiome composition associated with bacterial vaginosis or an individual not having a microbiome composition associated with bacterial vaginosis or both; and
identifying a classification of the presence or absence of the microbiome composition associated with bacterial vaginosis and/or determining the course of treatment for the individual human having the microbiome composition associated with bacterial vaginosis based on the comparing.

In embodiments described herein, reference is made to "bacteria" and "bacterial material" (e.g., DNA). Additionally or alternatively, other microorganisms and their material (e.g., DNA) can be detected, classified, and used in the methods and compositions described herein and thus every occurrence of "bacterial" or "bacterial material" or equivalents thereof apply equally to other microorganisms, including but not limited to archaea, unicellular eukaryotic organisms, viruses, or the combinations thereof.

In a second aspect, the present invention provides a method of determining a classification of occurrence of a microbiome indicative of, or associated with, a bacterial vaginosis issue or screening for the presence or absence of a microbiome indicative of bacterial vaginosis issue in an individual and/or determining a course of treatment for an individual human having a microbiome indicative of a bacterial vaginosis issue, the method comprising, providing a sample comprising bacteria (or at least one of the following microorganisms including: bacteria, archaea, unicellular eukaryotic organisms and viruses, or the combinations thereof) from the individual human; determining an amount(s) of one or more of the following in the sample: bacteria taxon or gene sequence corresponding to gene functionality as set forth in Table A; comparing the determined amount(s) to a disease signature having cut-off or probability values for amounts of the bacteria taxon and/or gene sequence for an individual having a microbiome indicative of a bacterial vaginosis issue or an individual not having a microbiome indicative of a bacterial vaginosis issue or both; and determining a classification of the presence or absence of the microbiome indicative of a bacterial vaginosis issue and/or determining the course of treatment for the individual human having the microbiome indicative of a bacterial vaginosis issue based on the comparing.

In some embodiments, the determining comprises preparing DNA from the sample and performing nucleotide sequencing of the DNA. In some embodiments, the determining comprises deep sequencing bacterial DNA from the sample to generate sequencing reads, receiving at a computer system the sequencing reads; and mapping, with the computer system, the reads to bacterial genomes to determine whether the reads map to a sequence from the bacterial taxon or gene sequence corresponding to gene functionality from Table A; and determining a relative amount of different sequences in the sample that correspond to a sequence from the bacteria taxon or gene sequence corresponding to gene functionality from Table A.

In some embodiments, the deep sequencing is random deep sequencing. In some embodiments, the deep sequencing comprises deep sequencing of, e.g., bacterial and/or archaeal, 16S rRNA coding sequences. In some embodiments, the method further comprises obtaining physiological, demographic or behavioral information from the individual human, wherein the disease signature comprises physiological, demographic or behavioral information; and the determining comprises comparing the obtained physiological, demographic or behavioral information to corresponding information in the disease signature. In some embodiments, the sample is a fecal, blood, saliva, cheek swab, urine or bodily fluid from the individual human. In some embodiments, the method further comprises determining that the individual human likely has a microbiome indicative of a bacterial vaginosis issue; and treating the individual human to ameliorate at least one symptom of the microbiome indicative of the bacterial vaginosis issue. In some embodiments, the treating comprises administering a dose of one of more of the bacteria taxon listed in Table A to the individual human for which the individual human is deficient.

In a third aspect, the present invention provides a method for determining a classification of the presence or absence of a microbiome indicative of a bacterial vaginosis issue and/or determine a course of treatment for an individual human having a microbiome indicative of a bacterial vaginosis issue, the method comprising performing, by a computer system: receiving sequence reads of bacterial DNA obtained from analyzing a test sample from the individual human; mapping the sequence reads to a bacterial sequence database to obtain a plurality of mapped sequence reads, the bacterial sequence database including a plurality of reference sequences of a plurality of bacteria; assigning the mapped sequence reads to sequence groups based on the mapping to obtain assigned sequence reads assigned to at least one sequence group, wherein a sequence group includes one or more of the plurality of reference sequences; determining a total number of assigned sequence reads; for each sequence group of a disease signature set of one or more sequence groups selected from TABLE A: determining a relative abundance value of assigned sequence reads assigned to the sequence group relative to the total number of assigned sequence reads, the relative abundance values forming a test feature vector; comparing the test feature vector to calibration feature vectors generated from relative abundance values of calibration samples having a known status of bacterial vaginosis; and determining the classification of the presence or absence of the microbiome indicative of a bacterial vaginosis issue and/or determining the course of treatment for the individual human having the microbiome indicative of a bacterial vaginosis issue based on the comparing.

In some embodiments, the comparing includes: clustering the calibration feature vectors into a control cluster not having the microbiome indicative of a bacterial vaginosis issue and a disease cluster having the microbiome indicative of a bacterial vaginosis issue; and determining which cluster the test feature vector belongs. In some embodiments, the clustering includes using a Bray-Curtis dissimilarity. In some embodiments, the comparing includes comparing each of the relative abundance values of the test feature vector to a respective cutoff value determined from the calibration feature vectors generated from the calibration samples. In some embodiments, the comparing includes: comparing a first relative abundance value of the test feature vector to a disease probability distribution to obtain a disease probability for the individual human having a microbiome indicative of a bacterial vaginosis issue, the disease probability distribution determined from a plurality of samples having the microbiome indicative of the bacterial vaginosis issue and exhibiting the sequence group; comparing the first relative abundance value to a control probability distribution to obtain a control probability for the individual human not having a microbiome indicative of a bacterial vaginosis issue, wherein the disease probabilities and the control probabilities are used to determine the classification of the presence or absence of the microbiome indicative of a bacterial vaginosis issue and/or determining the course of treatment for the individual human having the microbiome indicative of a bacterial vaginosis issue.

In some embodiments, the sequence reads are mapped to one or more predetermined regions of the reference sequences. In some embodiments, the disease signature set includes at least one taxonomic group and at least one functional group. In some embodiments, the analyzing comprises deep sequencing. In some embodiments, the deep sequencing reads are random deep sequencing reads. In some embodiments, the deep sequencing reads comprise 16S rRNA (e.g., bacterial and/or archaeal) deep sequencing reads. In some embodiments, the method further comprises receiving physiological, demographic or behavioral information from the individual human; and using the physiological, demographic or behavioral information in combination with the classification with the comparing of the test feature vector to the calibration feature vectors to determine the classification of the presence or absence of the microbiome indicative of a bacterial vaginosis issue and/or determining the course of treatment for the individual human having the microbiome indicative of a bacterial vaginosis issue. In some embodiments, the method further comprises preparing DNA from the sample and performing nucleotide sequencing of the DNA.

In a fourth aspect, the present invention provides a non-transitory computer readable medium storing a plurality of instructions that when executed, by the computer system, perform any one of the foregoing methods.

In a fifth aspect, the present invention provides a method for at least one of characterizing, diagnosing, and treating a bacterial vaginosis issue in at least a subject, the method comprising: •at a sample handling network, receiving an aggregate set of samples from a population of subjects; •at a computing system in communication with the sample handling network, generating a microbiome composition dataset and a microbiome functional diversity dataset for the population of subjects upon processing nucleic acid content of each of the aggregate set of samples with a fragmentation operation, a multiplexed amplification operation using a set of primers, a sequencing analysis operation, and an alignment operation; •at the computing system, receiving a supplementary dataset, associated with at least a subset of the population of subjects, wherein the supplementary dataset is informative of characteristics associated with the bacterial vaginosis issue; •at the computing system, transforming the supplementary dataset and features extracted from at least one of the microbiome composition dataset and the microbiome functional diversity dataset into a characterization model of the bacterial vaginosis issue; •based upon the characterization model, generating a therapy model configured to correct the bacterial vaginosis issue; and •at an output device associated with the subject and in communication with the computing system, promoting a therapy to the subject with the bacterial vaginosis issue, upon processing a sample from the subject with the characterization model, in accordance with the therapy model.

In some embodiments, generating the characterization model comprises performing a statistical analysis to assess a set of microbiome composition features and microbiome functional features having variations across a first subset of the population of subjects exhibiting the bacterial vaginosis issue and a second subset of the population of subjects not exhibiting the bacterial vaginosis issue. In some embodiments, generating the characterization model comprises:

•extracting candidate features associated with a set of functional aspects of microbiome components indicated in the microbiome composition dataset to generate the microbiome functional diversity dataset; and •characterizing the mental health issue in association with a subset of the set of functional aspects, the subset derived from at least one of clusters of orthologous groups of proteins features, genomic functional features from the Kyoto Encyclopedia of Genes and Genomes (KEGG), chemical functional features, and systemic functional features. In some embodiments, generating the characterization model of the bacterial vaginosis issue comprises generating a characterization that is diagnostic of at least one symptom of bacterial vaginosis. In some embodiments, generating the characterization that is diagnostic of at least one symptom of the bacterial vaginosis issue comprises generating the characterization upon processing the aggregate set of samples and determining presence of features derived from 1) a set of one or more taxa from Table A, and 2) a set of functions of Table A.

In a sixth aspect, the present invention provides a method for characterizing a bacterial vaginosis issue, the method comprising: •upon processing an aggregate set of samples from a population of subjects, generating at least one of a microbiome composition dataset and a microbiome functional diversity dataset for the population of subjects, the microbiome functional diversity dataset indicative of systemic functions present in the microbiome components of the aggregate set of samples; •at the computing system, transforming at least one of the microbiome composition dataset and the microbiome functional diversity dataset into a characterization model of the bacterial vaginosis issue, wherein the characterization model is diagnostic of the bacterial vaginosis issue producing observed changes in health, quality of life, or behavior; and •based upon the characterization model, generating a therapy model configured to improve a state of the bacterial vaginosis issue.

In some embodiments, generating the characterization comprises analyzing a set of features from the microbiome composition dataset with a statistical analysis, wherein the set of features includes features associated with: relative abundance of different taxonomic groups represented in the microbiome composition dataset, interactions between different taxonomic groups represented in the microbiome composition dataset, and phylogenetic distance between taxonomic groups represented in the microbiome composition dataset. In some embodiments, generating the characterization comprises performing a statistical analysis with at least one of a Kolmogorov-Smirnov test and a t-test to assess a set of microbiome composition features and microbiome functional features having varying degrees of abundance in a first subset of the population of subjects exhibiting the bacterial vaginosis issue and a second subset of the population of subjects not exhibiting the bacterial vaginosis issue, wherein generating the characterization further includes clustering using a Bray-Curtis dissimilarity.

In some embodiments generating the characterization model comprises generating a characterization that is diagnostic of at least one symptom of the bacterial vaginosis issue, upon processing the aggregate set of samples and determining presence of features derived from 1) a set of one or more taxa of Table A, and 2) a set of one or more functions of Table A. In some embodiments, the method further includes diagnosing a subject with the bacterial vaginosis issue upon processing a sample from the subject with the characterization model; and at an output device associated with the subject, promoting a therapy to the subject with the bacterial vaginosis issue based upon the characterization model and the therapy model. In some embodiments, promoting the therapy comprises promoting a bacteriophage-based therapy to the subject, the bacteriophage-based therapy providing a bacteriophage component that selectively downregulates a population size of an undesired taxon associated with the bacterial vaginosis issue.

In some embodiments, promoting the therapy comprises promoting a prebiotic therapy to the subject, the prebiotic therapy affecting a microorganism component that selectively supports a population size increase of a desired taxon associated with correction of the bacterial vaginosis issue, based on the therapy model. In some embodiments, promoting the therapy comprises promoting a probiotic therapy to the subject, the probiotic therapy affecting a microorganism component of the subject, in promoting correction of the bacterial vaginosis issue, based on the therapy model. In some embodiments, promoting the therapy comprises promoting a microbiome modifying therapy to the subject in order to improve a state of the bacterial vaginosis associated symptom.

DETAILED DESCRIPTION

Figure 1A:
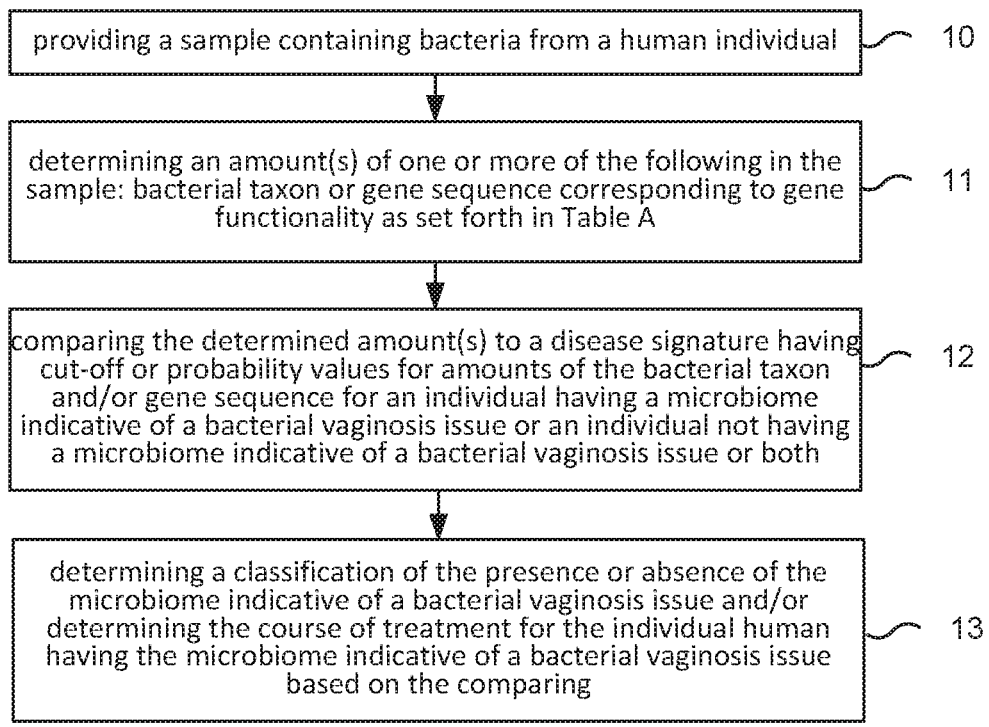
FIG. 1A is a flowchart of an embodiment of a method for determining a classification of the presence or absence of a bacterial vaginosis issue and/or determining the course of treatment for the individual human having a bacterial vaginosis issue.

The inventors have discovered that characterization of the microbiome of individuals is useful for detecting effects on the individuals' microbiomes due to bacterial vaginosis and identifying therapies that would have a positive effect in addressing one or more symptoms attributable to such bacterial vaginosis. For example, an individual having symptoms indicative of bacterial vaginosis, or in whom bacterial vaginosis is suspected, can be tested to confirm or provide further evidence to support or refute a finding of bacterial vaginosis in the subject. As another example, an individual having symptoms indicative of bacterial vaginosis, can be tested to determine the extent to which the microbiome is altered by the bacterial vaginosis. As another example, an individual having, or suspected of having, or having a history of, bacterial vaginosis can be assayed to determine whether the microbiome is likely to be a causative agent, or contribute to the frequency or severity of bacterial vaginosis. An individual having symptoms that are caused by bacterial vaginosis, or are likely to be caused by bacterial vaginosis, or has bacterial vaginosis, or has a microbiome (e.g., a gut, stool, or vaginal microbiome) that causes or contributes to the frequency or severity of bacterial vaginosis is referred to as having a "bacterial vaginosis issue."

Such characterizations are also useful for screening individuals for and/or determining a course of treatment for an individual has a bacterial vaginosis issue. For example, by deep sequencing bacterial DNAs from control (healthy, or at least not having a bacterial vaginosis issue) individuals and diseased individuals (having bacterial vaginosis), the inventors have discovered that the amount of certain bacteria and/or bacterial sequences corresponding to certain genetic pathways can be used to predict the presence or absence of a bacterial vaginosis issue. The bacteria and genetic pathways in some cases are present in a certain abundance in individuals having a bacterial vaginosis issue as discussed in more detail below whereas the bacteria and genetic pathways are at a statistically different abundance in control individuals that are do not have a bacterial vaginosis issue.

I. Bacteria Groups

Details of these associations can be found in TABLE A for bacteria groups (also called taxonomic groups) and or genetic pathways (also called functional groups). Collectively, the taxonomic groups and functional groups are referred to as features, or as sequence groups in the context of determining an amount of sequence reads corresponding to a particular group (feature). Scoring of a particular bacteria or genetic pathway can be determined according to a comparison of an abundance value to one or more reference (calibration) abundance values for known samples, e.g., where a detected abundance value less than a certain value is associated with a bacterial vaginosis issue and above the certain value is scored as associated with a lack of a bacterial vaginosis issue, depending on the particular criterion. Similarly, depending on the particular criterion, a detected abundance value greater than a certain value can be associated with a bacterial vaginosis issue and below the certain value can be scored as associated with a lack of a bacterial vaginosis issue or a microbiome that is not indicative of bacterial vaginosis. The scoring for various bacteria or genetic pathways can be combined to provide a classification for a subject.

TABLE A

| Group 2 | p-value | # disease subjects detected | # control subjects detected | Mean % abundance for disease | Mean % abundance for control |
| --- | --- | --- | --- | --- | --- |
| Bacterial vaginosis (87) vs none (365) Taxa (microbiome composition): Genus: | | | | | |
| *Lactobacillus*_1578 Family: | 3.94E−05 | 78 | 253 | 74.382 | 69.827 |
| Lactobacillaceae_33958 Order: | 3.45E−05 | 79 | 256 | 73.515 | 69.081 |
| Lactobacillales_186826 Function (microbiome functionality): KEGG L2: | 1.26E−04 | 87 | 339 | 70.117 | 56.298 |
| Membrane Transport | 7.16E−07 | 82 | 330 | 15.023 | 13.861 |
| Neurodegenerative Diseases | 9.77E−07 | 82 | 330 | 0.078 | 0.102 |
| Metabolism of Cofactors and Vitamins | 4.59E−06 | 82 | 330 | 3.279 | 3.802 |
| Signaling Molecules and Interaction | 2.07E−05 | 82 | 330 | 0.323 | 0.293 |
| Metabolism of Other Amino Acids | 3.70E−05 | 82 | 330 | 1.482 | 1.546 |
| Metabolism of Terpenoids and Polyketides | 7.97E−05 | 82 | 330 | 1.713 | 1.795 |
| Transcription | 1.95E−04 | 82 | 330 | 2.741 | 2.642 |
| Enzyme Families | 3.65E−04 | 82 | 330 | 2.469 | 2.386 |
| Amino Acid Metabolism | 6.42E−04 | 82 | 329 | 6.873 | 7.582 |
| Endocrine System | 7.72E−04 | 82 | 330 | 0.182 | 0.244 |

TABLE A-continued

| Group 2 | p-value | # disease subjects detected | # control subjects detected | Mean % abundance for disease | Mean % abundance for control |
|---|---|---|---|---|---|
| Biosynthesis of Other Secondary Metabolites | 1.32E−03 | 82 | 331 | 0.519 | 0.583 |
| Carbohydrate Metabolism | 1.36E−03 | 82 | 329 | 10.555 | 10.244 |
| Replication and Repair | 1.46E−03 | 82 | 330 | 11.332 | 10.973 |
| Transport and Catabolism | 1.56E−03 | 82 | 330 | 0.141 | 0.181 |
| KEGG L3: | | | | | |
| beta-Lactam resistance | 3.24E−08 | 80 | 319 | 0.047 | 0.037 |
| Starch and sucrose metabolism | 3.26E−08 | 80 | 319 | 1.101 | 0.993 |
| Dioxin degradation | 1.72E−07 | 80 | 319 | 0.144 | 0.115 |
| Phosphotransferase system (PTS) | 3.52E−07 | 80 | 319 | 1.431 | 1.148 |
| Lysine degradation | 3.79E−07 | 80 | 319 | 0.087 | 0.132 |
| Transporters | 6.63E−07 | 80 | 319 | 8.119 | 7.441 |
| Xylene degradation | 1.35E−06 | 80 | 319 | 0.100 | 0.081 |
| D-Alanine metabolism | 2.16E−06 | 80 | 319 | 0.218 | 0.194 |
| Valine, leucine and isoleucine degradation | 5.27E−06 | 80 | 319 | 0.185 | 0.249 |
| Energy metabolism | 5.54E−06 | 80 | 319 | 0.496 | 0.612 |
| Pentose phosphate pathway | 5.97E−06 | 80 | 319 | 0.980 | 0.925 |
| Penicillin and cephalosporin biosynthesis | 6.50E−06 | 80 | 319 | 0.047 | 0.039 |
| RNA polymerase | 1.41E−05 | 80 | 319 | 0.283 | 0.262 |
| Nicotinate and nicotinamide metabolism | 1.79E−05 | 80 | 319 | 0.442 | 0.477 |
| Photosynthesis | 2.10E−05 | 80 | 319 | 0.474 | 0.438 |
| Photosynthesis proteins | 2.20E−05 | 80 | 319 | 0.474 | 0.439 |
| Signal transduction mechanisms | 2.96E−05 | 80 | 319 | 0.634 | 0.570 |
| RNA transport | 3.40E−05 | 80 | 319 | 0.192 | 0.161 |
| Nitrogen metabolism | 3.43E−05 | 80 | 319 | 0.504 | 0.558 |
| Glycine, serine and threonine metabolism | 3.72E−05 | 80 | 319 | 0.568 | 0.657 |
| Tryptophan metabolism | 4.41E−05 | 80 | 319 | 0.143 | 0.178 |
| Folate biosynthesis | 5.47E−05 | 80 | 319 | 0.295 | 0.372 |
| Other transporters | 5.71E−05 | 80 | 319 | 0.138 | 0.167 |
| Glycolysis/Gluconeogenesis | 6.64E−05 | 80 | 319 | 1.614 | 1.483 |
| Bacterial secretion system | 8.01E−05 | 80 | 319 | 0.580 | 0.615 |
| Pores ion channels | 8.05E−05 | 80 | 319 | 0.172 | 0.727 |
| Galactose metabolism | 8.11E−05 | 80 | 319 | 0.851 | 0.755 |
| Amino sugar and nucleotide sugar metabolism | 9.03E−05 | 80 | 319 | 1.654 | 1.561 |
| Pantothenate and CoA biosynthesis | 9.70E−05 | 80 | 319 | 0.446 | 0.500 |
| Peptidases | 1.04E−04 | 80 | 319 | 2.249 | 2.159 |
| Oxidative phosphorylation | 1.58E−04 | 80 | 319 | 0.957 | 1.051 |
| Synthesis and degradation of ketone bodies | 1.83E−04 | 80 | 319 | 0.117 | 0.099 |
| Chromosome | 1.96E−04 | 80 | 319 | 1.797 | 1.717 |
| Transcription factors | 2.34E−04 | 80 | 319 | 1.683 | 1.563 |
| Histidine metabolism | 2.38E−04 | 80 | 319 | 0.212 | 0.308 |
| Protein folding and associated processing | 2.45E−04 | 80 | 319 | 0.489 | 0.589 |
| Glyoxylate and dicarboxylate metabolism | 2.52E−04 | 80 | 319 | 0.285 | 0.329 |
| Valine, leucine and isoleucine biosynthesis | 2.67E−04 | 80 | 319 | 0.309 | 0.388 |
| Porphyrin and chlorophyll metabolism | 3.23E−04 | 80 | 319 | 0.194 | 0.376 |
| Benzoate degradation | 3.36E−04 | 80 | 319 | 0.323 | 0.298 |
| ABC transporters | 3.96E−04 | 80 | 319 | 3.647 | 3.482 |
| Bacterial toxins | 4.83E−04 | 80 | 319 | 0.183 | 0.168 |
| Membrane and intracellular structural molecules | 5.37E−04 | 80 | 319 | 0.300 | 0.368 |
| DNA repair and recombination proteins | 5.72E−04 | 80 | 319 | 3.708 | 3.601 |
| Carbohydrate metabolism | 6.70E−04 | 80 | 319 | 0.127 | 0.118 |
| Cytoskeleton proteins | 8.28E−04 | 80 | 319 | 0.352 | 0.323 |
| Primary immunodeficiency | 9.26E−04 | 80 | 319 | 0.105 | 0.097 |
| Butanoate metabolism | 9.46E−04 | 80 | 319 | 0.513 | 0.554 |
| Inorganic ion transport and metabolism | 1.02E−03 | 80 | 319 | 0.108 | 0.132 |
| Nucleotide metabolism | 1.33E−03 | 80 | 319 | 0.095 | 0.085 |
| Peroxisome | 1.61E−03 | 80 | 319 | 0.109 | 0.140 |

The comparison of an abundance value to one or more reference abundance values can involve a comparison to a cutoff value determined from the one or more reference values. Such cutoff value(s) can be part of a decision tree or a clustering technique (where a cutoff value is used to determine which cluster the abundance value(s) belong) that are determined using the reference abundance values. The comparison can include intermediate determination of other values, e.g., probability values. The comparison can also include a comparison of an abundance value to a probability distribution of the reference abundance values, and thus a comparison to probability values.

The inventors have identified the specific bacteria taxa and genetic pathways listed in TABLE A by deep sequencing of bacterial DNA associated with samples from test individuals having a bacterial vaginosis issue and control individuals that do not have a bacterial vaginosis issue and determining those criteria that readily distinguish test individuals from control individuals. Deep sequencing allows for determination of a sufficient number of copies of DNA sequences to determine relative amount of corresponding bacteria or genetic pathways in the sample. Having identified the criteria in TABLE A, one can now detect an individual that has a bacterial vaginosis issue by detecting one or more (e.g., 2, 3, 4, 5, 6, 7, 8, 9, 10, 11, 12, 13, 14, 15, 16, 17, 18, 19, 20, 21, 22, 23, 24, 25, or more) of the options in TABLE A by any quantitative detection method. In some cases, one can now detect an individual that has a bacterial vaginosis issue by detecting from about 1 to about 20, from about 2 to about 15, from about 3 to about 10, from about 1 to about 10, from about 1 to about 15, from about 1 to about 5, or from about 5 to about 30 of the options in TABLE A by any quantitative detection method. For example, while deep sequencing can be used to detect the presence, absence or amount of one or more option in TABLE A, one can also use other detection methods, including but not limited to protein detection methods. For example, without intending to limit the scope of the invention, one could use protein-based diagnostics such as immunoassays to detect bacterial taxons by detecting taxon-specific protein markers.

As a result of these discoveries (e.g., as set forth in TABLE A), one can design treatments to ameliorate one or more symptoms of a bacterial vaginosis issue and/or alleviate or reduce the frequency and/or severity of bacterial vaginosis. As a non-limiting example, one can determine whether an individual having a bacterial vaginosis issue lacks, or has a reduced abundance of, one or more type of bacteria as listed in TABLE A and if so, that one or more type of bacteria can be administered to the individual. Additionally, or alternatively, one can determine whether an individual having a bacterial vaginosis issue lacks, or has a reduced abundance of, one or more type of bacteria as listed in TABLE A and if so, a pre-biotic that promotes the growth of that one or more type of bacteria can be administered to the individual. Additionally, or alternatively, one can determine whether an individual having a bacterial vaginosis issue has an increased abundance of one or more type of bacteria as listed in TABLE A and if so, a targeted therapy that reduces the abundance of such bacteria (e.g., bacteriophage therapy or selective antibiotic therapy) can be administered to the individual.

II. Determining Likelihood of a Bacterial Vaginosis Issue

In some embodiments, a method of determining whether, or the likelihood whether, an individual has a bacterial vaginosis issue is provided. As described herein, an individual having a bacterial vaginosis issue can exhibit an increase in one or more taxonomic groups in the microbiome, a decrease in one or more taxonomic groups in the microbiome, an increase in one or more functional groups in the microbiome, a decrease in one or more functional groups in the microbiome, or a combination thereof (e.g., relative to a control/healthy individual or population of control or healthy individuals).

The method can include one or more of the following steps:

obtaining a sample from the individual;

purifying nucleic acids (e.g., DNA) from the sample;

deep sequencing nucleic acids from the sample so as to determine the amount of one or more (e.g., 2, 3, 4, 5, 6, 7, 8, 9, 10, 11, 12, 13, 14, 15, 16, 17, 18, 19, 20, or more, e.g., 1-20, 2-15, 3-10, 1-10, 1-15, 1-5, or 5-30) of the features listed in TABLE. A; and comparing the resulting amount of each feature to one or more reference amounts of the one or more of the features listed in TABLE A as occurs in an average individual having a bacterial vaginosis issue or an individual not having a bacterial vaginosis issue or both. The compilation of features can sometimes be referred to as a "disease signature" for a specific disease (i.e., a bacterial vaginosis issue) or a "condition signature" for a specific condition. The disease signature can act as a characterization model, and may include probability distributions for control population (no bacterial vaginosis issue) or disease populations having the disease (a bacterial vaginosis issue) or both. The disease signature can include one or more of the features (e.g., bacterial taxa or genetic pathways) in TABLE A and can optionally include criteria determined from abundance values of the control and/or disease populations. Example criteria can include cutoff or probability values for amounts of those features associated with average control individuals (no bacterial vaginosis issue) or individuals having the disease (a bacterial vaginosis issue).

The likelihood of an individual having a microbiome indicative of a bacterial vaginosis issue (e.g., as listed in TABLE A) refers to the chance (degree of confidence) that the results from the individual's sample can be correlated with a bacterial vaginosis issue. Alternatively, one can simply screen for a bacterial vaginosis issue, i.e., one can generate a yes or no indication for the presence or absence of a microbiome indicative of a bacterial vaginosis issue. In some embodiments, the individual will not yet have been diagnosed with bacterial vaginosis or a symptom caused by bacterial vaginosis. In other examples, the individual can have been initially diagnosed by other methods and the methods described herein can be used to provide better (or worse) confidence of the initial diagnosis.

Any type of sample containing bacteria can be used from the individual. Exemplary sample types include, for example, a fecal sample, blood sample, saliva sample, cheek swab, urine or other bodily fluid from the individual. Nucleic acids (e.g., DNA and/or RNA) can be purified from the sample. Basic texts disclosing the general molecular biology methods include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994-1999). Such nucleic acids may also be obtained through in vitro amplification methods such as those described herein and in Berger, Sambrook, and Ausubel, as well as Mullis et al., (1987) U.S. Pat. No. 4,683,202; *PCR Protocols A Guide to Methods and Appli-* cations (Innis et al., eds) Academic Press Inc. San Diego, Calif. (1990) (Innis); Arnheim & Levinson (Oct. 1, 1990) C&EN 36-47; *The Journal Of NIH Research* (1991) 3: 81-94; Kwoh et al. (1989) *Proc. Natl. Acad. Sci. USA* 86: 1173; Guatelli et al. (1990) *Proc. Natl. Acad. Sci. USA* 87, 1874; Lomeli et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117, each of which is incorporated by reference in its entirety for all purposes and in particular for all teachings related to amplification methods. In some embodiments, the nucleic acids will not be amplified before they are quantified.

Any of a variety of detection methods can be used to screen an individual's sample for one or more of the features listed in TABLE A. For example, in some embodiments, nucleic acid hybridization and/or amplification methods are used to detect and quantify one or more of the features. In some embodiments, an immunoassay or other assay to detect and quantify one or more specific proteins determinative of one or more of the criteria can be used. For example, solid-phase ELISA immunoassays, Western blots, or immunohistochemistry are routinely used to specifically detect a protein. See. Harlow and Lane *Antibodies, A Laboratory Manual*, Cold Spring Harbor Publications, NY (1988) for a description of immunoassay formats and conditions that can be used to determine specific immunoreactivity. In some preferred embodiments, nucleotide sequencing is used to identify and quantify one or more of the criteria.

DNA sequencing can be performed as desired. Such sequencing can be performed using known sequencing methodologies, e.g., Illumina, Life Technologies, and Roche 454 sequencing systems. In typical embodiments, a sample is sequenced using a large-scale sequencing method that provides the ability to obtain sequence information from many reads. Such sequencing platforms include those commercialized by Roche 454 Life Sciences (GS systems), Illumina (e.g., HiSeq, MiSeq) and Life Technologies (e.g., SOLiD systems).

The Roche 454 Life Sciences sequencing platform involves using emulsion PCR and immobilizing DNA fragments onto bead. Incorporation of nucleotides during synthesis is detected by measuring light that is generated when a nucleotide is incorporated.

The Illumina technology involves the attachment of genomic DNA to a planar, optically transparent surface. Attached DNA fragments are extended and bridge amplified to create an ultra-high density sequencing flow cell with clusters containing copies of the same template. These templates are sequenced using a sequencing-by-synthesis technology that employs reversible terminators with removable fluorescent dyes.

Methods that employ sequencing by hybridization may also be used. Such methods, e.g., used in the Life Technologies SOLiD4+ technology uses a pool of all possible oligonucleotides of a fixed length, labeled according to the sequence. Oligonucleotides are annealed and ligated; the preferential ligation by DNA ligase for matching sequences results in a signal informative of the nucleotide at that position.

The sequence can be determined using any other DNA sequencing method including, e.g., methods that use semiconductor technology to detect nucleotides that are incorporated into an extended primer by measuring changes in current that occur when a nucleotide is incorporated (see, e.g., U.S. Patent Application Publication Nos. 20090127589 and 20100035252). Other techniques include direct label-free exonuclease sequencing in which nucleotides cleaved from the nucleic acid are detected by passing through a nanopore (Oxford Nanopore) (Clark et al., *Nature Nanotechnology* 4: 265-270, 2009); and Single Molecule Real Time (SMRT™) DNA sequencing technology (Pacific Biosciences), which is a sequencing-by synthesis technique.

Deep sequencing can be used to quantify the number of copies of a particular sequence in a sample and then also be used to determine the relative abundance of different sequences in a sample. Deep sequencing refers to highly redundant sequencing of a nucleic acid sequence, for example such that the original number of copies of a sequence in a sample can be determined or estimated. The redundancy (i.e., depth) of the sequencing is determined by the length of the sequence to be determined (X), the number of sequencing reads (N), and the average read length (L). The redundancy is then N×L/X. The sequencing depth can be, or be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 110, 120, 130, 150, 200, 300, 500, 500, 700, 1000, 2000, 3000, 4000, 5000 or more. See, e.g., Mirebrahim, Hamid et al., *Bioinformatics* 31 (12): i9-i16 (2015).

In some embodiments, specific sequences in the sample can be targeted for amplification and/or sequencing. For example, specific primers can be used to detect and sequence bacterial sequences of interest. Exemplary target sequences can include, but are not limited to, the 16S rRNA coding sequence (e.g., gene families mentioned in the discussion of Block S120), as well as gene sequences involved in one or more genetic pathway as shown in TABLE A. In addition, or alternatively, whole genome sequencing methods that randomly sequence DNA fragments in a sample can be used.

Once sequencing raw data is generated, the resulting sequence reads can be "mapped" to known sequences in a genomic database. Exemplary algorithms that are suitable for determining percent sequence identity and sequence similarity and thus aligning and identifying sequence reads are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. Accordingly, for the sequence reads generated, a subset of these reads will be aligned to one or more bacterial genomes of the bacterial taxa in Table A or can be aligned to a gene sequence in any genome that has a genetic function as set forth in Tables A. For example, one can align a read with a database of bacterial sequences and the read can be designated as from a particular bacteria if that read has the best alignment to a DNA sequence from that bacteria in the database.

Similarly, one can align a read with a database of bacterial sequences and the read can be designated as from a genetic pathway if that read has the best alignment to a DNA sequence from that genetic pathway in the database. For example, one can assign the read to a sequence from a particular Kyoto Encyclopedia of Genes and Genomes (KEGG) category or Clusters of Orthologous Groups (COG) categories. KEGGs are described more at genome.jp/kegg/. COGs are described in, e.g., Tatusov, et al., *Nucleic Acids Res.* 2000 Jan. 1; 28(1): 33-36. The TABLE provided herein lists various KEGG and COG categories that are correlated with the presence or absence of a microbiome indicative of a bacterial vaginosis issue. Different levels of KEGG or COG categories are provided in TABLE A. Values in Table A for particular criteria are proportional values compared to totals at that taxonomic or functional designation level.

Assuming sequencing has occurred at a sufficient depth, one can quantify the number of reads for sequences indicative of the presence of a feature of TABLE A, thereby allowing one to set a value for an estimated amount of one of the criterion. The number of reads or other measures of amount of one of the features can be provided as an absolute or relative value. An example of an absolute value is the number of reads of 16S rRNA coding sequence reads that map to the genus of *Bacteroides*. Alternatively, relative amounts can be determined. An exemplary relative amount calculation is to determine the amount of 16S rRNA coding sequence reads for a particular bacterial taxon (e.g., genus, family, order, class, or phylum) relative to the total number of 16S rRNA coding sequence reads assigned to the bacterial domain. A value indicative of amount of a feature in the sample can then be compared to a cut-off value or a probability distribution in a disease signature for a microbiome indicative of a bacterial vaginosis issue. For example, if the signature indicates that a relative amount of feature #1 of 50% or more of all features possible at that level indicates the likelihood of a microbiome indicative of a bacterial vaginosis issue, then quantification of gene sequences associated with feature #1 less than 50% in a sample would indicate a higher likelihood of a microbiome that is not indicative of a bacterial vaginosis issue and alternatively, quantification of gene sequences associated with feature #1 more than 50% in a sample would indicate a higher likelihood of a microbiome indicative of a bacterial vaginosis issue.

Once amounts of various features from TABLE A have been determined and compared to a cut-off or probability value for the corresponding criteria in a disease signature for a bacterial vaginosis issue, one can determine the likelihood of a microbiome indicative of a bacterial vaginosis issue in the individual.

Disease signatures can include criteria corresponding to one or at least one of the features set forth in TABLE A. In some embodiments, 2, 3, 4, 5, 6, 7, 8, 9, 10, 11, 12, 13, 14, 15, 16, 17, 18, 19, 20 or more (e.g., all) of the criteria of TABLE A can be used in a disease signature for a microbiome indicative of a bacterial vaginosis issue.

In some embodiments, supplementary information about the individual can also be used in the disease signature and thus also for determining the likelihood of occurrence of a microbiome indicative of a bacterial vaginosis issue in the individual. Supplementary information can include, for example, different demographics (e.g., genders, ages, marital statuses, ethnicities, nationalities, socioeconomic statuses, sexual orientations, etc.), different health conditions (e.g., health and disease states), different living situations (e.g., living alone, living with pets, living with a significant other, living with children, etc.), different dietary habits (e.g., omnivorous, vegetarian, vegan, sugar consumption, acid consumption, etc.), different behavioral tendencies (e.g., levels of physical activity, drug use, alcohol use, etc.), different levels of mobility (e.g., related to distance traveled within a given time period), biomarker states (e.g., cholesterol levels, lipid levels, etc.), weight, height, body mass index, genotypic factors, and any other suitable trait that has an effect on microbiome composition.

FIG. 1A is a flowchart of an embodiment of a method for determining a classification of the presence or absence of a microbiome indicative of a bacterial vaginosis issue or indicative of bacterial vaginosis and/or determining the course of treatment for the individual human having the microbiome indicative of a bacterial vaginosis issue or indicative of bacterial vaginosis.

At block 10, a sample comprising bacteria from the individual human is provided. In specific examples, samples can comprise blood samples, saliva samples, plasma/serum samples (e.g., to enable extraction of cell-free DNA), cerebrospinal fluid, and tissue samples. In some cases, the sample is a vaginal sample (e.g., a vaginal swab, smear, or swipe), or a sample (e.g., a nucleic acid sample, such as a DNA sample) extracted from a vaginal sample.

At block 11, an amount(s) of bacteria taxon and/or gene sequence corresponding to gene functionality as set forth in Table A is determined. As various examples, an amount of one bacteria taxon can be determined; an amount of one gene sequence corresponding to gene functionality can be determined; an amount of one bacteria taxon and an amount one gene sequence corresponding to gene functionality can be determined; multiple amounts (e.g., 2-6) of bacteria taxa can be determined; multiple amounts (e.g., 2-6) of gene sequences corresponding to gene functionalities can be determined; and multiple amounts of both can be determined.

The amount can be determined in various ways, e.g., by sequencing nucleic acids in the sample, using a hybridization array, and PCR. As examples, the amounts can correspond to levels of a signal or a count of numbers of nucleic acids corresponding to each taxa. The amount can be a relative abundance value.

At block 12, the determined amount(s) are compared to a condition signature having cut-off or probability values for amounts of the bacteria taxon and/or gene sequence for an individual having a microbiome indicative of a bacterial vaginosis issue or an individual not having a microbiome indicative of a bacterial vaginosis issue or both. In various embodiments, each amount can be compared to a separate value, and a number of taxa exceeding that value can be compared to a threshold for determining whether a sufficient number of the taxa provide the condition signature. Other examples are provider herein. Before a comparison to a probability value, the amount can be transformed (e.g., via a probability distribution). As another example, the amounts can be used to determine a measure probability, which can be compared to the probability value, which discriminates among classifications.

At block 13, a classification of the presence or absence of the microbiome indicative of a bacterial vaginosis issue is determined based on the comparing, and/or the course of treatment for the individual human having the microbiome indicative of a bacterial vaginosis issue is determined based on the comparing. As described herein, the classification can be binary or includes more levels, e.g., corresponding to a probability.

III. Treatment of Issues Related to the Disease

Also provided are methods of determining a course of treatment, and/or optionally of treating, an individual having a microbiome indicative of a bacterial vaginosis issue. For example, by detecting the presence, absence, or quantity of one or more of the criteria set forth in TABLE A, one can determine treatments to increase those criteria that are reduced in individuals having a condition/disease (i.e., individuals having a microbiome indicative of a bacterial vaginosis issue) or decrease these criteria that are increased in individuals having the disease (a bacterial vaginosis issue) compared to healthy individuals (i.e., individuals having a microbiome that is not indicative of a bacterial vaginosis issue). In some embodiments, the individual will have been diagnosed, optionally by other methods, of having a microbiome associated with a bacterial vaginosis issue, or symptoms thereof, and the methods described herein (e.g., comparison to the disease signature) will reveal excessive amounts and/or deficient amounts of one or more of the features that can then be used to guide treatment.

For example, in embodiments in which the amount of a particular bacteria type is lower in individuals having a microbiome indicative of a bacterial vaginosis issue than in individuals having a microbiome that is not indicative of a bacterial vaginosis issue, a possible treatment is providing a probiotic or prebiotic treatment that provides or stimulates growth of the particular bacteria type.

In embodiments in which the higher amount of bacteria is in the individual having a microbiome indicative of a bacterial vaginosis issue, one can administer treatments that reduce the relative amount of that particular bacteria. In some embodiments, antibiotics can be administered to reduce the target bacterial population. Alternatively, other treatments can be administered including promoting (by administration of probiotics or prebiotics) bacteria that compete with the target bacteria. In yet another embodiment, bacteriophage targeting the particular bacteria can be administered to the individual.

Similarly, where a particular function (e.g., KEGG or COG category) is indicated, one can increase or reduce that function by selectively promoting or reducing growth of bacterial populations that have that particular function.

Figure 5:
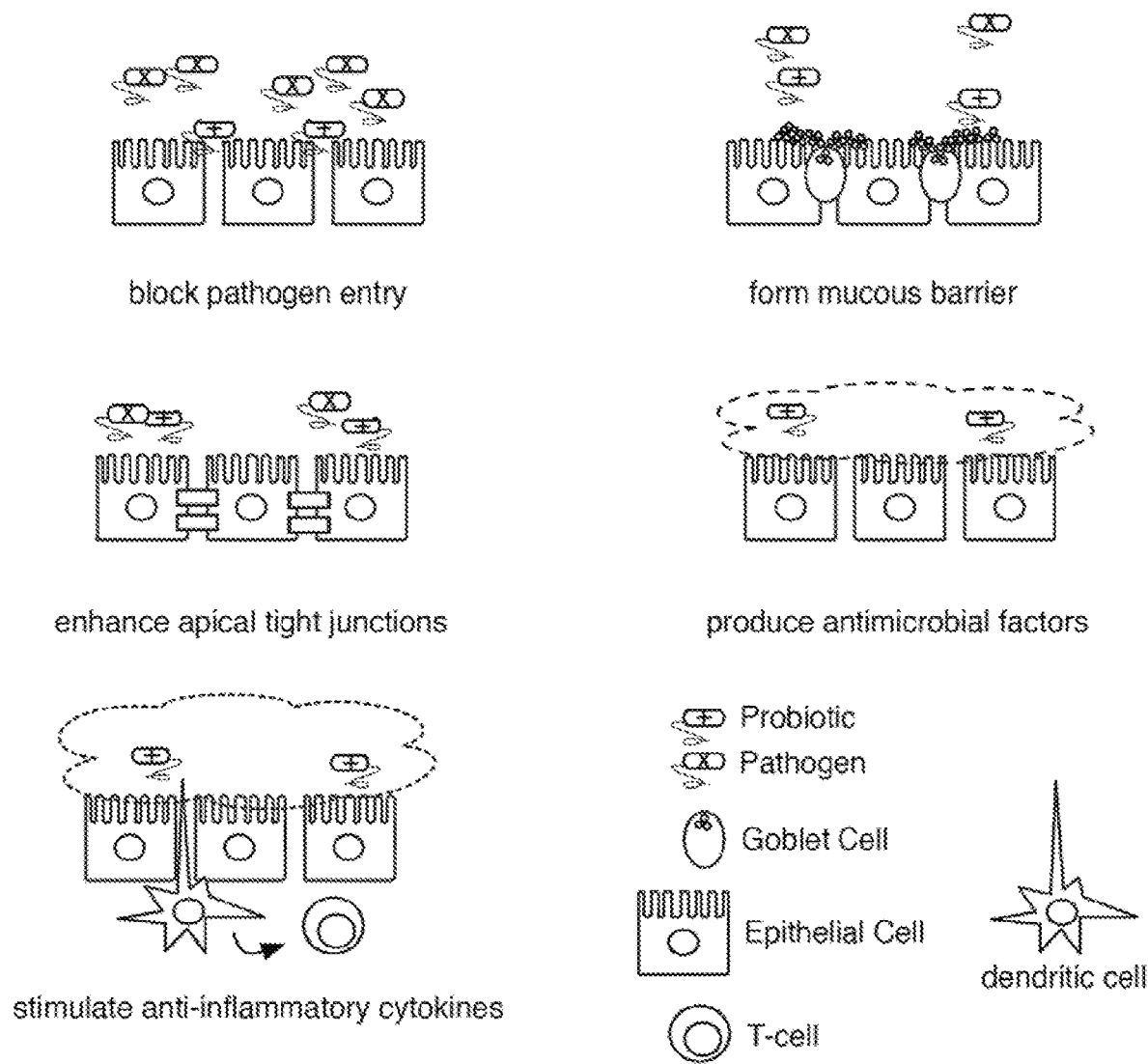
FIG. 5 depicts variations of mechanisms by which therapies probiotic-based or prebiotic-based therapies) operate in an embodiment of a method for characterizing a health condition.

Additional mechanisms of treatment are listed, for example, in FIG. 5.

Further, one can monitor treatment of an individual having a microbiome indicative of a bacterial vaginosis issue by obtaining samples from the individual before, during, and/or after treatment of the bacterial vaginosis issue, or before, during, and/or after treatment to mitigate the symptoms of a bacterial vaginosis issue (e.g., pre-biotic, pro-biotic, or bacteriophage therapy), or the combination thereof, to monitor progression of the bacterial vaginosis issue. For example, in some embodiments, levels of one or more of the criteria in TABLE A are determined one or more (e.g., 2 or more, 3, 4, 5 or more) times and the dosage of a pre-biotic and/or pro-biotic treatment can be adjusted up or down depending on how the criteria respond to the treatment.

IV. Analysis of Sequence Information

In some embodiments, sequence information can be received. The sequence information can correspond to one or more sequence reads per nucleic acid molecule (e.g., a DNA fragment). The sequence reads can be obtained in a variety of ways. For example, a hybridization array, PCR, or sequencing techniques can be used.

When sequencing is performed, a sequence read can be aligned (mapped) to a plurality of reference bacterial genomes (also called reference genomes) to determine which reference bacterial genome the sequence read aligns and where on that reference genome the sequence read aligns. The alignment can be to a particular region (e.g., 16S region) of a reference genome, and thus to a reference sequence, which can be all or part of the reference genome. For paired-end sequencing, both sequence reads can be aligned as a pair, with an expected length of the nucleic acid molecule being used to aid in the alignment.

Accordingly, it can be determined that a particular DNA fragment is derived from a particular gene of a particular bacterial taxonomic group (also called taxon) based on the aligned location of a sequence read to the particular gene of the particular bacterial taxonomic group.

The same determination may be made by various hybridization probes using a variety of techniques, as will be known by one skilled in the art. Thus, the mapping can be performed in a variety of ways.

In this manner, a count of the number of sequence reads aligned to each of one or more genes of different bacterial taxonomic groups can be determined. The count for each gene and for each taxonomic group can be used to determine relative abundances. For example, a relative abundance value (RAV) of a particular taxonomic group can be determined based on a fraction (proportion) of sequence reads aligning to that taxonomic group relative to other taxonomic groups. The RAV can correspond to the proportion of reads assigned to a particular taxonomic or functional group. The proportion can be relative to various denominator values, e.g., relative to all of the sequence reads, relative to all assigned to at least one group (taxonomic or functional), or all assigned to for a given level in the hierarchy. The alignment can be implemented in any manner that can assign a sequence read to a particular taxonomic or functional group. For example, based on the mappings to the reference sequence(s) in the 16S region, a taxonomic group with the best match for the alignment can be identified. The RAV can then be determined for that taxonomic group using the number of sequence reads (or votes of sequence reads) for a particular sequence group divided by the number of sequence reads identified as being bacterial, which may be for a specific region or even for a given level of a hierarchy.

A taxonomic group can include one or more bacteria and their corresponding reference sequences. A taxonomic group can correspond to any set of one or more reference sequences for one or more loci (e.g., genes) that represent the taxonomic group. Any given level of a taxonomic hierarchy would include a plurality of taxonomic groups. For instance, a reference sequence in the one group at the genus level can be in another group at the family level. A sequence read can be assigned based on the alignment to a taxonomic group when the sequence read aligns to a reference sequence of the taxonomic group. A functional group can correspond to one or more genes labeled as having a similar function. Thus, a functional group can be represented by reference sequences of the genes in the functional group, where the reference sequences of a particular gene can correspond to various bacteria. The taxonomic and functional groups can collectively be referred to as sequence groups, as each group includes one or more reference sequences that represent the group. A taxonomic group of multiple bacteria can be represented by multiple reference sequence, e.g., one reference sequence per bacteria species in the taxonomic group. Embodiments can use the degree of alignment of a sequence read to multiple reference sequences to determine which sequence group to assign the sequence read based on the alignment.

As mentioned above, a particular genomic region (e.g., gene 16S) can be analyzed. For example, the region can be amplified, and a portion of the amplified DNA fragments can be sequenced. The amplification can be to such a degree that most reads will correspond to the amplified region. Other example regions can be smaller than a gene, e.g., variable regions within a gene. The longer the region, more resolution can be obtained to determine voting to assign a sequence read to a group. Multiple non-contiguous regions can be analyzed, e.g., by amplifying multiple regions.

A. Example Determination of Relative Abundance of a Sequence Group (Feature)

As mentioned above, a relative abundance value can correspond to a proportion of sequence reads that align to at least one reference sequence of a sequence group, also referred to as a feature herein. A sequence read can be assigned to one or more sequence groups based on the alignment to the reference sequence(s) for each sequence group. A sequence read can be assigned to more than one sequence group if the assigned groups are in different categories (e.g., taxonomic or functional) or in different levels of a hierarchy (e.g., genus and family). And, a sequence group can include multiple sequences for different regions or a same region, e.g., a sequence group can include more than one base at a particular position, e.g., if the group encompasses various polymorphisms at a genomic position. A sequence group is an example of a feature that can be used to characterize a sample, e.g., when the sequence group has a statistically significant separation between the control population and the disease population.

1. Assignment to a Sequence Group

In some embodiments, sequence reads can be obtained for two ends of a nucleic acid molecule, e.g., via paired-end sequencing. Embodiments can identify whether each sequence read of a pair of sequence reads corresponds to a particular sequence group. Each sequence read can effectively have a vote, and the nucleic acid molecule can be identified as corresponding to a particular sequence group only if both sequence reads are aligned to that sequence group (alignment may allow mismatches when less than 100% sequence identity is used). In such embodiments, molecules that do not have both sequence reads aligning to the same sequence group can be discarded. The alignment to a reference sequence may be required to be perfect (i.e., no mismatches), while other embodiments can allow mismatches. Further, the alignment can be required to be unique, or else the read is discarded.

In other embodiments, a partial vote can be attributed to each sequence group to which a sequence read aligns. In one implementation, a weight of the partial vote based on the degree of alignment, e.g., whether there are any mismatches. In other implementations, each sequence read can get a vote when it does exist in a reference sequence, and that vote is weighted by the probability of its existence in humans. A total weight for a read being assigned to a particular reference sequence can be determined by various factors, each providing a weight. The total votes to the reference sequence of a group can be determined and compared to the total votes for other groups in the same level. For each read, the sequence group at a given level with the highest percentage for assignment to the read can be assigned the read. Various techniques of partial assignment can be used, e.g., Dirichlet partial assignment.

Sequencing can be advantageous for assigning sequence reads to a group, as sequencing provides the actual sequence of at least a portion of a nucleic acid molecule. The sequence might be slightly different than what has already been known for a particular taxonomic group, but it may be similar enough to assign to a particular taxonomic group. If predetermined probes were used, then that nucleic acid molecule might not be identified. Thus, one can identify unknown bacteria, but whose sequence is similar enough to an existing taxonomic group, or even assigned to an unknown group.

In some embodiments, the proportion can be the total of sequence reads, even if some are not assigned, or equivalently assigned to an unknown group. As an example, the 16S gene can be analyzed, and a read can be determined to align to one or more reference sequences in the region, e.g., with a certain number of mismatches below a threshold, but with a high enough variations to not correspond to any known taxonomic group (or functional group as discussed below). Thus, embodiments can include unassigned reads that contribute to the denominator for determining the proportion of reads of a certain sequence group relative to the sequence reads identified as being bacterial. Thus, a proportion of the bacterial population of sequence reads can be determined. Using predetermined probes would generally not allow one to identify unknown bacterial sequences.

2. Sequence Group Corresponds to a Particular Taxonomic Group

A taxonomic group can correspond to any set of one or more reference sequences for one or more loci (e.g., genes) that represent the taxonomic group. Any given level of a taxonomic hierarchy would include a plurality of taxonomic groups. The taxonomic groups of a given level of the taxonomic hierarchy would typically be mutually exclusive. Thus, a reference sequence of one taxonomic group would not be included in another taxonomic group in the same level. For example, a reference sequence in one group at the genus level would not be included in another group at the genus level. But, that reference sequence in the one group at the genus level can be in another group at the family level.

The RAV can correspond to the proportion of reads assigned to a particular taxonomic group. The proportion can be relative to various denominator values, e.g., relative to all of the sequence reads, relative to all assigned to at least one group (taxonomic or functional), or all assigned to for a given level in the hierarchy. The alignment can be implemented in any manner that can assign a sequence read to a particular taxonomic group.

For example, based on the mappings to the reference sequence(s) in the 16S region, a taxonomic group with the best match for the alignment can be identified. The RAV can then be determined for that taxonomic group using the number of sequence reads (or votes of sequence reads) for a particular sequence group divided by the number of sequence reads identified as being bacterial, which may be for a specific region or even for a given level of a hierarchy.

3. Sequence Group Corresponds to a Particular Gene or Functional Group

Instead of or in addition to determining a count of the sequence reads that correspond to a particular taxonomic group, embodiments can use a count of a number of sequence reads that correspond to a particular gene or a collection of genes having an annotation of a particular function, where the collection is called a functional group. The RAV can be determined in a similar manner as for a taxonomic group. For example, functional group can include a plurality of reference sequences corresponding to one or more genes of the functional group. Reference sequences of multiple bacteria for a same gene can correspond to a same functional group. Then, to determine the RAV, the number of sequence reads assigned to the functional group can be used to determine a proportion for the functional group.

The use of a function group, which may include a single gene, can help to identify situations where there is a small change (e.g., increase) in many taxonomic groups such that the change is too small to be statistically significant. But, the changes may all be for a same gene or set of genes of a same functional group, and thus the change for that functional group can be statistically significant, even though the changes for the taxonomic groups may not be significant. The reverse can be true of a taxonomic group being more predictive than a particular functional group, e.g., when a single taxonomic group includes many genes that have change by a relatively small amount.

As an example, if 10 taxonomic groups increase by 10%, the statistical power to discriminate between the two groups may be low when each taxonomic group is analyzed individually. But, if the increase is all for genes(s) of a same functional group, then the increase would be 100%, or a doubling of the proportion for that taxonomic group. This large increase would have a much larger statistical power for discriminating between the two groups. Thus, the functional group can act to provide a sum of small changes for various taxonomic groups. And, small changes for various functional groups, which happen to all be on a same taxonomic group, can sum to provide high statistical power for that particular taxonomic group.

The taxonomic groups and functional groups can supplement each other as the information can be orthogonal, or at least partially orthogonal as there still may be some relationship between the RAVs of each group. For example, the RAVs of one or more taxonomic groups and functional groups can be used together as multiple features of a feature vector, which is analyzed to provide a diagnosis, as is described herein. For instance, the feature vector can be compared to a disease signature as part of a characterization model.

B. Example Determination of Statistically Significant Separation of Abundance of a Sequence Group Between Control and Disease Populations Embodiments can use the relative abundance values (RAVs) for populations of subjects that have a disease (condition population; i.e., individuals having a microbiome indicative of a bacterial vaginosis issue) and that do not have the disease (control population; i.e., individuals having a microbiome that is not indicative of a bacterial vaginosis issue). If the distribution of RAVs of a particular sequence group for the disease population is statistically different than the distribution of RAVs for the control population, then the particular sequence group can be identified for including in a disease signature. Since the two populations have different distributions, the RAV for a new sample for a sequence group in the disease signature can be used to classify (e.g., determine a probability) of whether the sample does or does not have the disease. The classification can also be used to determine a treatment, as is described herein. A discrimination level can be used to identify sequence groups that have a high predictive value. Thus, embodiment can filter out taxonomic groups that are not very accurate for providing a diagnosis.

1. Discrimination Level of Sequence Group

Once RAVs of a sequence group have been determined for the control and condition populations, various statistical tests can be used to determine the statistical power of the sequence group for discriminating between a bacterial vaginosis issue (condition) and no bacterial vaginosis issue (control). In one embodiment, the Kolmogorov-Smirnov (KS) test can be used to provide a probability value (p-value) that the two distributions are actually identical. The smaller the p-value the greater the probability to correctly identify which population a sample belongs. The larger the separation in the mean values between the two populations generally results in a smaller p-value (an example of a discrimination level). Other tests for comparing distributions can be used. The Welch's t-test presumes that the distributions are Gaussian, which is not necessarily true for a particular sequence group. The KS test, as it is a non-parametric test, is well suited for comparing distributions of taxa or functions for which the probability distributions are unknown.

The distribution of the RAVs for the control and condition populations can be analyzed to identify sequence groups with a large separation between the two distributions. The separation can be measured as a p-value (See example section). For example, the relative abundance values for the control population may have a distribution peaked at a first value with a certain width and decay for the distribution. And, the disease population can have another distribution that is peaked a second value that is statistically different than the first value. In such an instance, an abundance value of a control sample has a lower probability to be within the distribution of abundance values encountered for the disease samples. The larger the separation between the two distributions, the more accurate the discrimination is for determining whether a given sample belongs to the control population or the disease population. As is discussed later, the distributions can be used to determine a probability for an RAV as being in the control population and determine a probability for the RAV being in the disease population.

Figure 7:
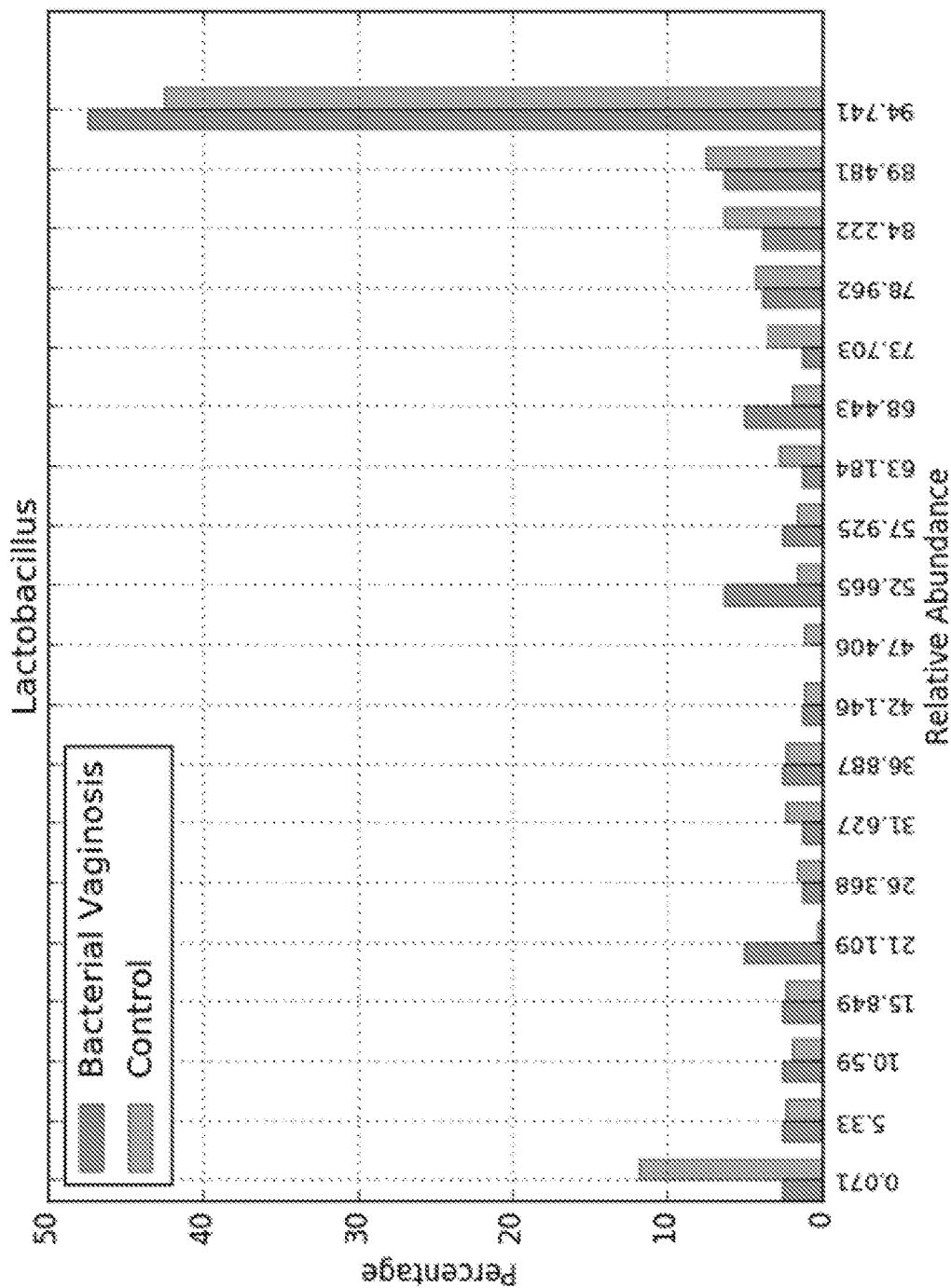
FIG. 7 depicts example data associated with a method for generating microbiome-derived diagnostics and therapeutics.
Figure 8:
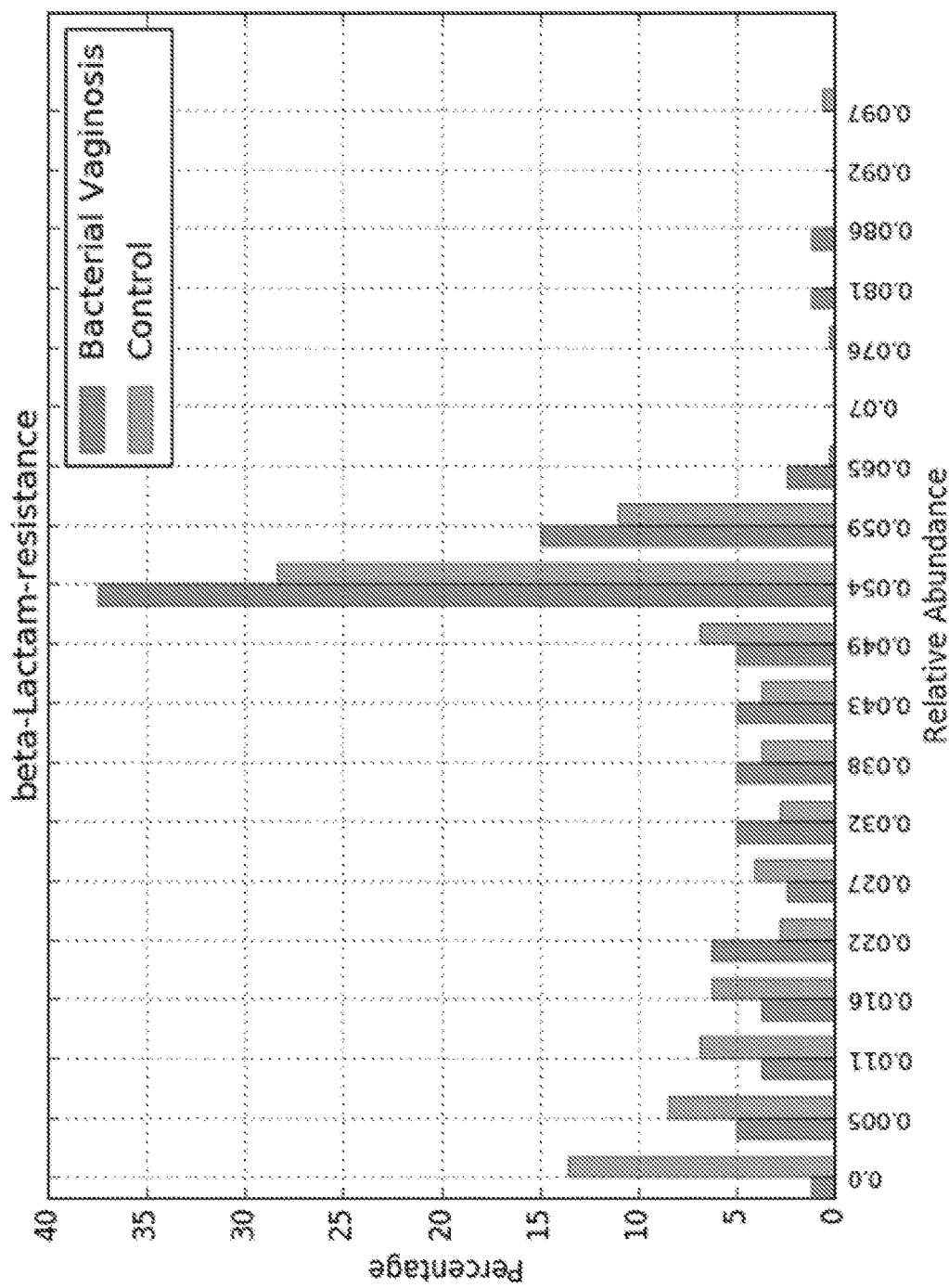
FIG. 8 depicts example data associated with a method for generating microbiome-derived diagnostics and therapeutics.

FIG. 7 shows a plot illustrating the control distribution and the disease distribution for a bacterial vaginosis issue where the sequence group is *Lactobacillus* for the genus taxonomic group according to embodiments of the present invention. As one can see, the RAVs for the disease group having a microbiome indicative of a bacterial vaginosis issue tend to have higher values than the control distribution. Thus, if *Lactobacillus* is present, a higher RAV would have a higher probability of being in the bacterial vaginosis issue population. The p-value in this instance is $3.94 \times 10^{-5}$, as indicated in Table A. FIG. 8 shows a similar plot illustrating the control distribution and the disease distribution for a bacterial vaginosis issue where the sequence group is the KEGG L3 functional group "beta-Lactam-resistance" according to embodiments of the present invention. The p-value in this instance is $3.24 \times 10^{-8}$, as indicated in Table A.

One of skill in the art will appreciate that, in some cases, the RAVs for the disease having a microbiome indicative of a bacterial vaginosis issue can have lower values than the control distribution. For example, the RAVs of the KEGG L2 group "neurodegenerative diseases" for the disease group tend to have lower values than the control group. Thus, if the KEGG L2 group "neurodegenerative diseases" is present, a lower RAV would have a higher probability of being in the bacterial vaginosis issue population. The p-value in this instance is $9.77 \times 10^{-7}$, as indicated in Table A.

2, Prevalence of Sequence Group in Population

In some embodiments, certain samples may not have any presence of a particular taxonomic group, or at least not a presence above a relatively low threshold (i.e., a threshold below either of the two distributions for the control and condition population). Thus, a particular sequence group may be prevalent in the population, e.g., more than 30% of the population may have the taxonomic group. Another sequence group may be less prevalent in the population, e.g., showing up in only 5% of the population. The prevalence (e.g., percentage of population) of a certain sequence group can provide information as to how likely the sequence group may be used to determine a diagnosis.

In such an example, the sequence group can be used to determine a status of the disease (e.g., diagnose for the disease) when the subject falls within the 30%. But, when the subject does not fall within the 30%, such that the taxonomic group is simply not present, the particular taxonomic group may not be helpful in determining a diagnosis of the subject. Thus, whether a particular taxonomic group or functional group is useful in diagnosing a particular subject can be dependent on whether nucleic acid molecules corresponding to the sequence group are actually sequenced.

Accordingly, the disease signature can include more sequence groups that are used for a given subject. As an example, the disease signature can include 100 sequence groups, but only 60 of sequence groups may be detected in a sample. The classification of the subject (including any probability for being in the application) would be determined based on the 60 sequence groups.

C. Example Generation of Characterization Model

The sequence groups with high discrimination levels (e.g., low p-values) for a given condition (e.g., a bacterial vaginosis issue) can be identified and used as part of a characterization model, e.g., which uses a disease signature to determine a probability of a subject having the disease. The disease signature can include a set of sequence groups as well as discriminating criteria (e.g., cutoff values and/or probability distributions) used to provide a classification of the subject. The classification can be binary (e.g., indicative of a bacterial vaginosis issue or not indicative of a bacterial vaginosis issue) or have more classifications (e.g., probability of being indicative of a bacterial vaginosis issue or not being indicative of a bacterial vaginosis issue). Which sequence groups of the disease signature that are used in making a classification be dependent on the specific sequence reads obtained, e.g., a sequence group would not be used if no sequence reads were assigned to that sequence group. In some embodiments, a separate characterization model can be determined for different populations, e.g., by geography where the subject is currently residing (e.g., country, region, or continent), the generic history of the subject (e.g., ethnicity), or other factors.

1. Selection of Sequence Groups

As mentioned above, sequence groups having at least a specified discrimination level can be selected for inclusion in the characterization model. In various embodiments, the specified discrimination level can be an absolute level (e.g., having a p-value below a specified value), a percentage (e.g., being in the top 10% of discriminating levels), or a specified number of the top discrimination levels (e.g., the top 100 discriminating levels). In some embodiments, the characterization model can include a network graph, where each node in a graph corresponds to a sequence group having at least a specified discrimination level.

The sequence groups used in a disease signature of a characterization model can also be selected based on other factors. For example, a particular sequence group may only be detected in a certain percentage of the population, referred to as a coverage percentage. An ideal sequence group would be detected in a high percentage of the population and have a high discriminating level (e.g., a low p-value). A minimum percentage may be required before adding the sequence group to the characterization model for a particular disease (e.g., a bacterial vaginosis issue). The minimum percentage can vary based on the accompanying discriminating level. For instance, a lower coverage percentage may be tolerated if the discriminating level is higher. As a further example, 95% of the patients with a disease may be classified with one or a combination of a few sequence groups, and the 5% remaining can be explained based on one sequence group, which relates to the orthogonality or overlap between the coverage of sequence groups. Thus, a sequence group that provides discriminating power for 5% of the individuals having the disease (e.g., a bacterial vaginosis issue) may be valuable.

Another factor for determining which sequence to include in a disease signature of the characterization model is the overlap in the subjects exhibiting the sequence groups of a disease signature. For example, to sequence groups can both have a high coverage percentage, but sequence groups may cover the exact same subjects. Thus, adding one of the sequence groups does increase the overall coverage of the disease signature. In such a situation, the two sequence groups can be considered parallel to each other. Another sequence group can be selected to add to the characterization model based on the sequence group covering different subjects than other sequence groups already in the characterization model. Such a sequence group can be considered orthogonal to the already existing sequence groups in the characterization model.

As examples, selecting a sequence group may consider the following factors. A taxa may appear in 100% of control individuals and in 100% of individuals having a specified disease (e.g., a bacterial vaginosis issue), but where the distributions are so close in both groups, that knowing the relative abundance of that taxa only allows to catalogue a few individuals as having the disease or lacking the disease (i.e. it has a low discriminating level). Whereas, a taxa that appears in only 20% of individuals not having the disease and 30% of individuals having the disease can have distributions of relative abundance that are so different from one another, it allows to catalogue 20% of individuals not having the disease and 30% of individuals having the disease (i.e. it has a high discriminating level).

In some embodiments, machine learning techniques can allow the automatic identification of the best combination of features (e.g., sequence groups). For instance, a Principal Component Analysis can reduce the number of features used for classification to only those that are the most orthogonal to each other and can explain most of the variance in the data. The same is true for a network theory approach, where one can create multiple distance metrics based on different features and evaluate which distance metric is the one that best separates individuals having the disease (a bacterial vaginosis issue) from individuals that do not have the disease.

2. Discrimination Criteria Sequence Groups

The discrimination criteria for the sequence groups included in the disease signature of a characterization model can be determined based on the disease distributions and the control distributions for the disease. For example, a discrimination criterion for a sequence group can be a cutoff value that is between the mean values for the two distributions. As another example, discrimination criteria for a sequence group can include probability distributions for the control and disease populations. The probability distributions can be determined in a separate manner from the process of determining the discrimination level.

The probability distributions can be determined based on the distribution of RAVs for the two populations. The mean values (or other average or median) for the two populations can be used to center the peaks of the two probability distributions. For example, if the mean RAV of the disease population is 20% (or 0.2), then the probability distribution for the disease population can have its peak at 20%. The width or other shape parameters (e.g., the decay) can also be determined based on the distribution of RAVs for the disease population. The same can be done for the control population.

D. Use of Sequence Groups

The sequence groups included in the disease signature of the characterization can be used to classify a new subject. The sequence groups can be considered features of the feature vector, or the RAVs of the sequence groups considered as features of a feature vector, where the feature vector can be compared to the discriminating criteria of the disease signature. For instance, the RAVs of the sequence groups for the new subject can be compared to the probability distributions for each sequence group of the disease signature. If an RAV is zero or nearly zero, then the sequence group may be skipped and not used in the classification.

The RAVs for sequence groups that are exhibited in the new subject can be used to determine the classification. For example, the result (e.g., a probability value) for each exhibited sequence group can be combined to arrive at the final classification. As another example, clustering of the RAVs can be performed, and the clusters can be used to determine a classification of a disease.

1. Classification of Disease Using Sequence Groups

Figure 1B:
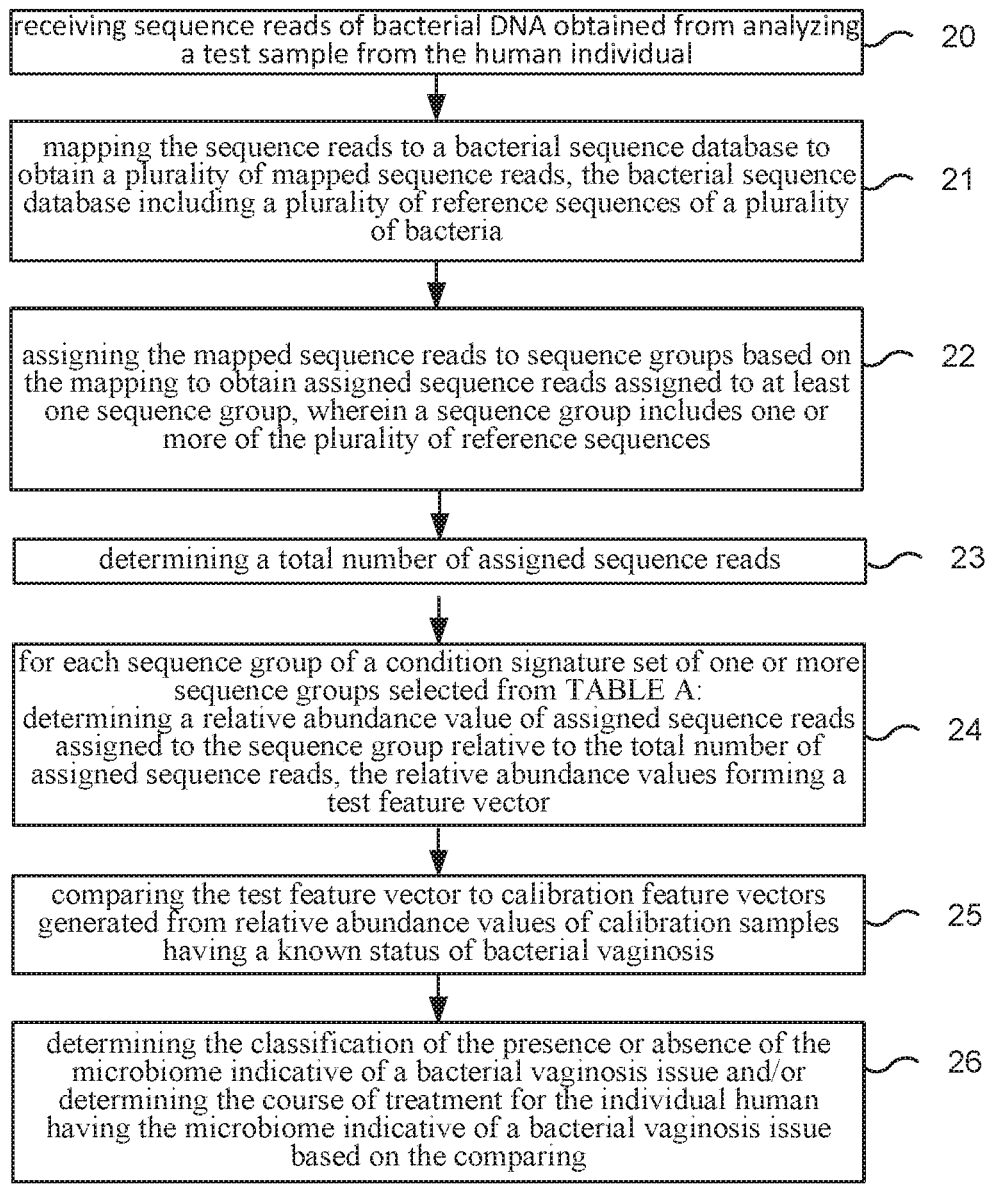
FIG. 1B is a flowchart of an embodiment of a method for determining a classification of the presence or absence of a bacterial vaginosis issue and/or determining the course of treatment for an individual human having a bacterial vaginosis issue.

Embodiments can provide a method for determining a classification of the presence or absence for a disease and/or determine a course of treatment for an individual human having the disease (a bacterial vaginosis issue). The method can be performed by a computer system, as described herein. FIG. 1B is a flowchart of an embodiment of a method for determining a classification of the presence or absence of a microbiome indicative of a bacterial vaginosis issue and/or determining the course of treatment for an individual human having the microbiome indicative of a bacterial vaginosis issue.

In block 20, sequence reads of bacterial DNA obtained from analyzing a test sample from the individual human are received. The analysis can be done with various techniques, e.g., as described herein, such as sequencing or hybridization arrays. The sequence reads can be received at a computer system, e.g., from a detection apparatus, such as a sequencing machine that provides data to a storage device (which can be loaded into the computer system) or across a network to the computer system.

In block 21, the sequence reads are mapped to a bacterial sequence database to obtain a plurality of mapped sequence reads. The bacterial sequence database includes a plurality of reference sequences of a plurality of bacteria. The reference sequences can be for predetermined region(s) of the bacteria, e.g., the 16S region.

In block 22, the mapped sequence reads are assigned to sequence groups based on the mapping to obtain assigned sequence reads assigned to at least one sequence group. A sequence group includes one or more of the plurality of reference sequences. The mapping can involve the sequence reads being mapped to one or more predetermined regions of the reference sequences. For example, the sequence reads can be mapped to the 16S gene. Thus, the sequence reads do not have to be mapped to the whole genome, but only to the region(s) covered by the reference sequences of a sequence group.

In block 23, a total number of assigned sequence reads is determined. In some embodiments, the total number of assigned reads can include reads identified as being bacterial, but not assigned to a known sequence group. In other embodiments, the total number can be a sum of sequence reads assigned to known sequence groups, where the sum may include any sequence read assigned to at least one sequence group.

In block 24, relative abundance value(s) can be determined. For example, for each sequence group of a disease signature set of one or more sequence groups selected from TABLE A, a relative abundance value of assigned sequence reads assigned to the sequence group relative to the total number of assigned sequence reads can be determined. The relative abundance values can form a test feature vector, where each values of the test feature vector is an RAV of a different sequence group.

In block 25, the test feature vector is compared to calibration feature vectors generated from relative abundance values of calibration samples having a known status of the disease. The calibration samples may be samples of a disease population and samples of a control population. In some embodiments, the comparison can involve various machine learning techniques, such as supervised machine learning (e.g. decision trees, nearest neighbor, support vector machines, neural networks, naïve Bayes classifier, etc. . . . ) and unsupervised machine learning (e.g., clustering, principal component analysis, etc. . . . ).

In one embodiment, clustering can use a network approach, where the distance between each pair of samples in the network is computed based on the relative abundance of the sequence groups that are relevant for each disease. Then, a new sample can be compared to all samples in the network, using the same metric based on relative abundance, and it can be decided to which cluster it should belong. A meaningful distance metric would allow all individuals having the disease (a bacterial vaginosis issue) to form one or a few clusters and all individuals lacking the disease to form one or a few clusters. One distance metric is the Bray-Curtis dissimilarity, or equivalently a similarity network, where the metric is 1 Bray-Curtis dissimilarity. Another example distance metric is the Tanimoto coefficient.

In some embodiments, the feature vectors may be compared by transforming the RAVs into probability values, thereby forming probability vectors. Similar processing for the feature vectors can be performed for the probability, with such a process still involving a comparison of the feature vectors since the probability vectors are generated from the feature vectors.

Block 26 can determine a classification of the presence or absence of the disease (e.g., a bacterial vaginosis issue) and/or determine a course of treatment for an individual human having the disease based on the comparing. For example, the cluster to which the test feature vector is assigned may be a disease cluster, and the classification can be made that the individual human has the disease or a certain probability for having the disease.

In one embodiment involving clustering, the calibration feature vectors can be clustered into a control cluster not having the disease and a disease cluster having the disease. Then, which cluster the test feature vector belongs can be determined. The identified cluster can be used to determine the classification or select a course of treatment. In one implementation, the clustering can use a Bray-Curtis dissimilarity.

In one embodiment involving a decision tree, the comparison may be performed to by comparing the test feature vector to one or more cutoff values (e.g., as a corresponding cutoff vector), where the one or more cutoff values are determined from the calibration feature vectors, thereby providing the comparison. Thus, the comparing can include comparing each of the relative abundance values of the test feature vector to a respective cutoff value determined from the calibration feature vectors generated from the calibration samples. The respective cutoff values can be determined to provide an optimal discrimination for each sequence group.

2. Use of Probability Values

A new sample can be measured to detect the RAVs for the sequence groups in the disease signature. The RAV for each sequence group can be compared to the probability distributions for the control and disease populations for the particular sequence group. For example, the probability distribution for the disease population can provide an output of a probability (disease probability) of having the disease for a given input of the RAV. Similarly the probability distribution for the control population can provide an output of a probability (control probability) of not having the disease for a given input of the RAV. Thus, the value of the probability distribution at the RAV can provide the probability of the sample being in each of the populations. Thus, it can be determined which population the sample is more likely to belong to, by taking the maximum probability.

In some embodiments, just the maximum probability is used in further steps of a characterization process. In other embodiments, both the disease probability and the control probability are used. As noted above, the probability distributions used here for classification may be different than the statistical test used to determine whether the distribution of RAV values are separated, e.g., the KS test.

A total probability across sequence groups of a disease signature can be used. For all of the sequence groups that are measured, a disease probability can be determined for whether the sample is in the disease group and a control probability can be determined for whether the sample is in the control population. In other embodiments, just the disease probabilities or just the control probabilities can be determined.

The probabilities across the sequence groups can be used to determine a total probability. For example, an average of the disease probabilities can be determined, thereby obtaining a final disease probability of the subject having the disease based on the disease signature. An average of the control probabilities can be determined, thereby obtaining a final control probability of the subject not having the disease based on the disease signature.

In one embodiment, the final disease probability and final control probability can be compared to each other to determine the final classification. For instance, a difference between the two final probabilities can be determined, and a final classification probability determined from the difference. A large positive difference with final disease probability being higher would result in a higher final classification probability of the subject having the disease.

In other embodiments, only the final disease probability can be used to determine the final classification probability. For example, the final classification probability can be the final disease probability. Alternatively, the final classification probability can be one minus the final control probability, or 100% minus the final control probability depending on the formatting of the probabilities.

In some embodiments, a final classification probability for one disease of a class can be combined with other final classification probabilities of other disease of the same class. The aggregated probability can then be used to determine whether the subject has at least one of the class of diseases. Thus, embodiments can determine whether a subject has a health issue that may include a plurality of diseases associated with that health issue.

The classification can be one of the final probabilities. In other examples, embodiments can compare a final probability to a threshold value to make a determination of whether the disease exists. For example, the respective disease probabilities can be averaged, and an average can be compared to a threshold value to determine whether the disease exists. As another example, the comparison of the average to the threshold value can provide a treatment for treating the subject.

V. Additional Embodiments

Described herein, and with reference to the FIGs, are additional illustrative embodiments of the methods, compositions, and systems provided herein. It will be appreciated that one of ordinary skill in the art can readily determine where and when any one or more of the methods, compositions, and/or systems described above can be utilized additionally, or alternatively, in the embodiments described below.

Figure 1C:
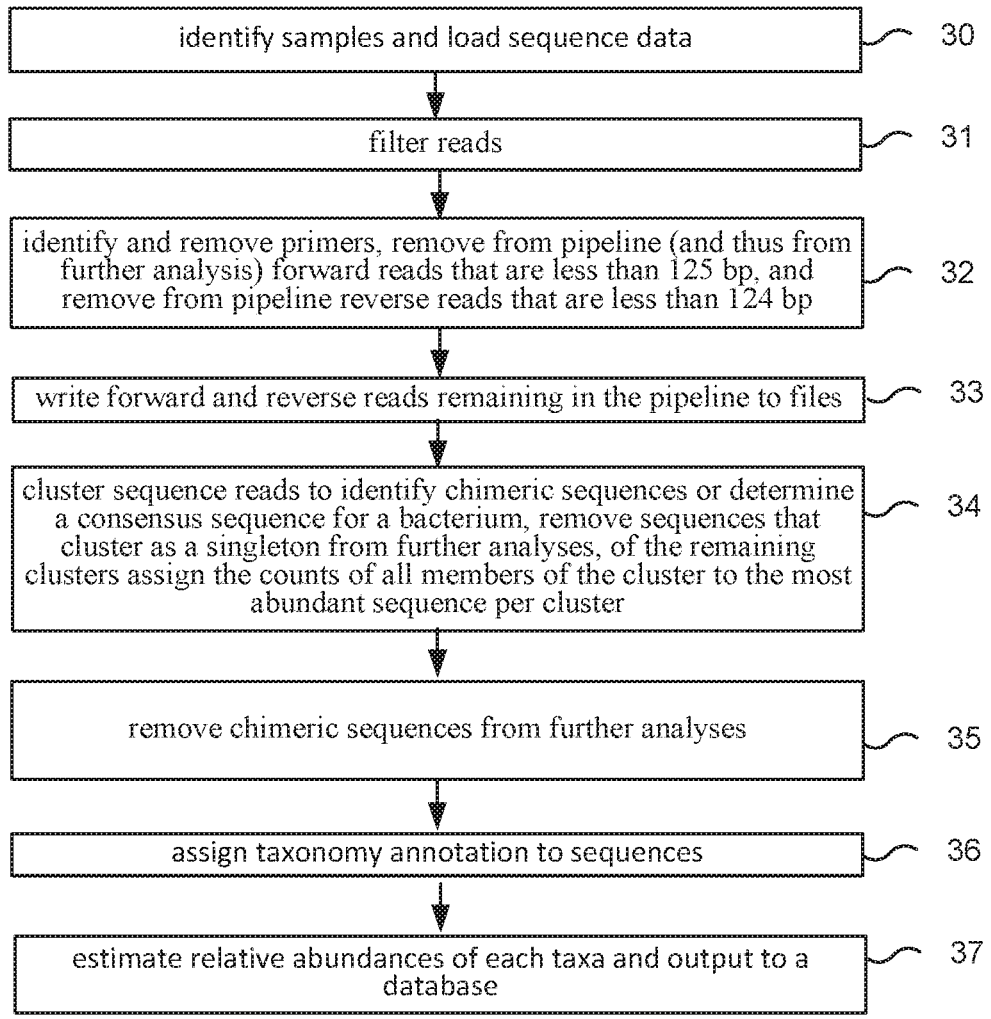
FIG. 1C is a flowchart of an embodiment of a method for estimating the relative abundances of a plurality of taxa from a sample and outputting the estimates to a database.
Figure 1D:
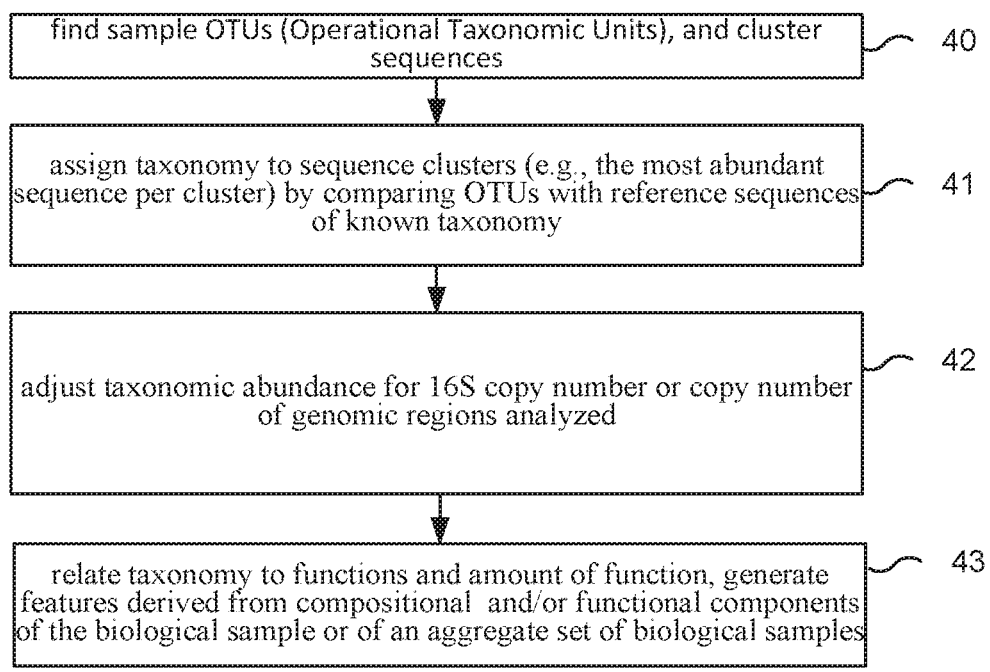
FIG. 1D is a flowchart of an embodiment of a method for generating features derived from composition and/or functional components of a biological sample or an aggregate of biological samples.
Figure 1E:
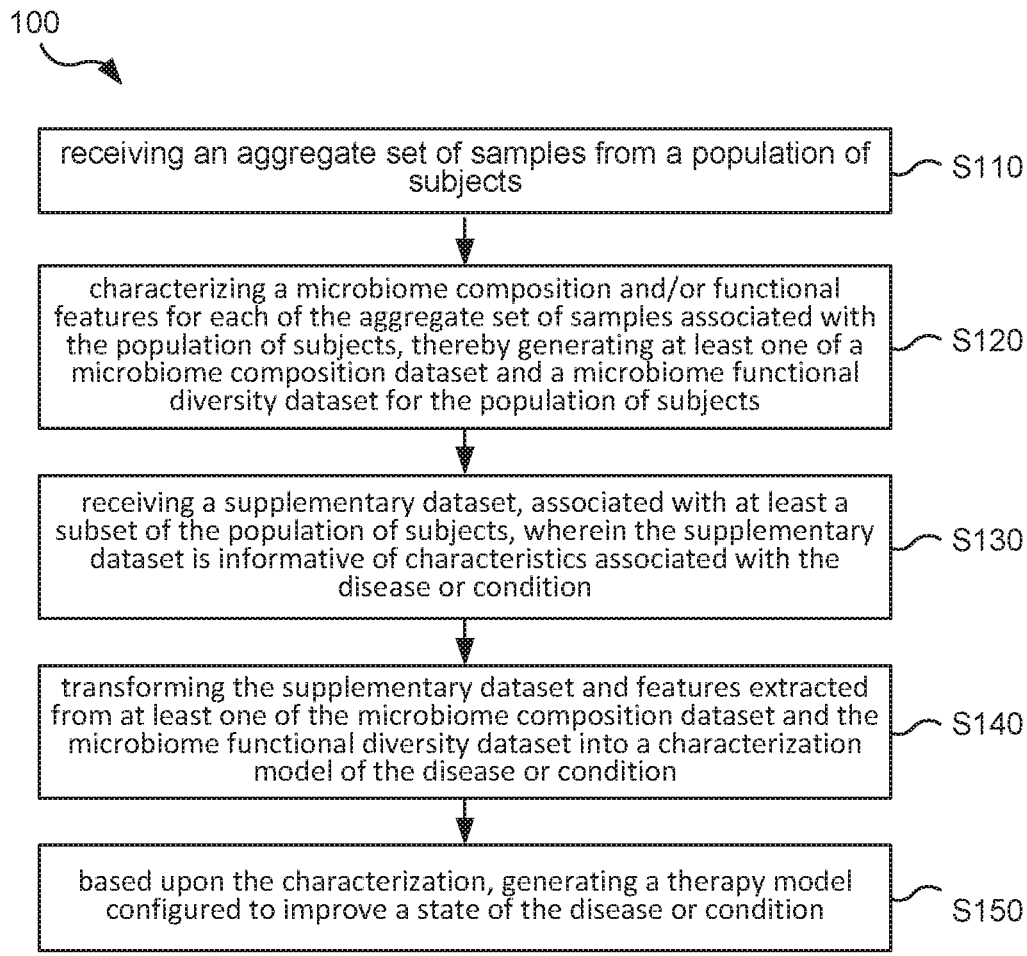
FIG. 1E is a flowchart of an embodiment of a method for characterizing a microbiome-associated condition and identifying therapeutic measures.

As shown in FIG. 1E, a first method 100 for diagnosing and treating an individual having a microbiome indicative of a bacterial vaginosis issue can comprise: receiving an aggregate set of samples from a population of subjects S110; characterizing a microbiome composition and/or functional features for each of the aggregate set of samples associated with the population of subjects, thereby generating at least one microbiome composition dataset, at least one microbiome functional diversity dataset, or a combination thereof, for the population of subjects S120. In some cases, the method can further comprise: receiving a supplementary dataset, associated with at least a subset of the population of subjects, wherein the supplementary dataset is informative of characteristics associated with a bacterial vaginosis issue S130. Typically, the method further comprises: and transforming the features extracted from the at least one microbiome composition dataset, microbiome functional diversity dataset, or the combination thereof, into a characterization model of a bacterial vaginosis issue S140. In some cases, the transforming includes transforming the supplementary dataset, if received. In some variations, the first method 100 can further include: based upon the characterization, generating a therapy model configured to improve health or condition of an individual having a bacterial vaginosis issue S150.

The first method 100 functions to generate models that can be used to characterize and/or diagnose subjects according to at least one of their microbiome composition and functional features (e.g., as a clinical diagnostic, as a companion diagnostic, etc.), and provide therapeutic measures (e.g., probiotic-based therapeutic measures, phage-based therapeutic measures, small-molecule-based therapeutic measures, prebiotic-based therapeutic measures, clinical measures, etc.) to subjects based upon microbiome analysis for a population of subjects. As such, data from the population of subjects can be used to characterize subjects according to their microbiome composition and/or functional features, indicate states of health and areas of improvement based upon the characterization(s), and promote one or more therapies that can modulate the composition of a subject's microbiome toward one or more of a set of desired equilibrium states.

In variations, the method 100 can be used to promote targeted therapies to subjects having a microbiome indicative of a bacterial vaginosis issue, wherein the bacterial vaginosis issue produces observed differences in at least one of social behavior, motor behavior, and energy levels, gastrointestinal heath, etc. In these variations, diagnostics associated with a bacterial vaginosis issue can be typically assessed using one or more of: a behavioral survey instrument, a motor skills based assessment, a blood cell analysis of a biological sample, a vaginal swab, swipe, or smear, and any other standard tool. As such, the method 100 can be used to characterize the effects of a bacterial vaginosis issue, including disorders, and/or adverse states in an entirely non-typical method. In particular, the inventors propose that characterization of the microbiome of individuals can be useful for predicting the likelihood of a bacterial vaginosis issue in subjects. Such characterizations can also be useful for screening for issues related to a bacterial vaginosis issue and/or determining a course of treatment for an individual human having a microbiome indicative of a bacterial vaginosis issue. For example, by deep sequencing bacterial DNAs from subjects having a bacterial vaginosis issue and control subjects, the inventors propose that features associated with certain microbiome compositional and/or functional features (e.g., the amount of certain bacteria and/or bacterial sequences corresponding to certain genetic pathways) can be used to predict the presence or absence of a microbiome indicative of a bacterial vaginosis issue. The bacteria and genetic pathways in some cases are present in a certain abundance in individuals having a microbiome indicative of a bacterial vaginosis issue as discussed in more detail below whereas the bacteria and genetic pathways are at a statistically different abundance in individuals not having a microbiome indicative of a bacterial vaginosis issue.

Figure 1F:
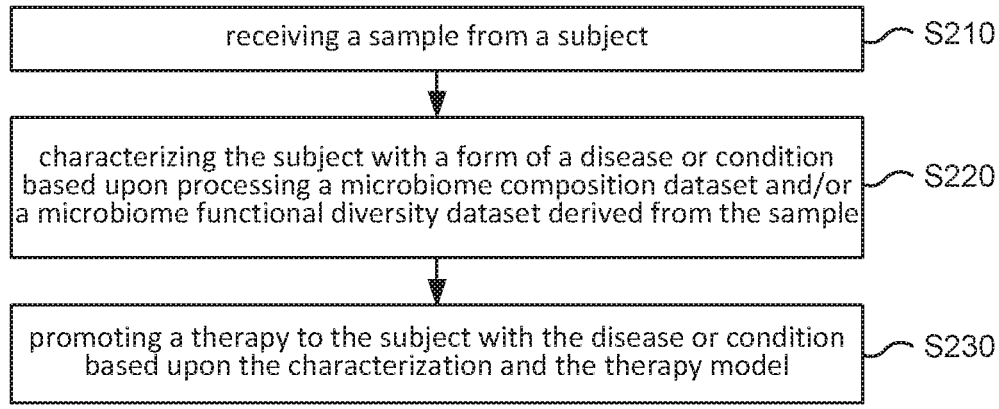
FIG. 1F is a flow chart of an embodiment of a method for generating microbiome-derived diagnostics.

As such, in some embodiments, outputs of the first method 100 can be used to generate diagnostics and/or provide therapeutic measures for a subject based upon an analysis of the subject's microbiome composition and/or functional features of the subject's microbiome. Thus, as shown in FIG. 1F, a second method 200 derived from at least one output of the first method 100 can include: receiving a biological sample from a subject S210; characterizing the subject as having or not having a microbiome indicative of a bacterial vaginosis issue based upon processing a microbiome dataset derived from the biological sample S220; and promoting a therapy to the subject with the microbiome indicative of a bacterial vaginosis issue based upon the characterization and the therapy model S230. Variations of the method 200 can further facilitate monitoring and/or adjusting of therapies provided to a subject, for instance, through reception, processing, and analysis of additional samples from a subject throughout the course of therapy. Embodiments, variations, and examples of the second method 200 are described in more detail below.

Thus, methods 100 and/or 200 can function to generate models that can be used to classify individuals and/or provide therapeutic measures (e.g., therapy recommendations, therapies, therapy regimens, etc.) to individuals based upon microbiome analysis for a population of individuals. As such, data from the population of individuals can be used to generate models that can classify individuals according to their microbiome compositions (e.g., as a diagnostic measure), indicate states of health and areas of improvement based upon the classification(s), and/or provide therapeutic measures that can push the composition of an individual's microbiome toward one or more of a set of improved equilibrium states. Variations of the second method 200 can further facilitate monitoring and/or adjusting of therapies provided to an individual, for instance, through reception, processing, and analysis of additional samples from an individual throughout the course of therapy.

Figure 2:
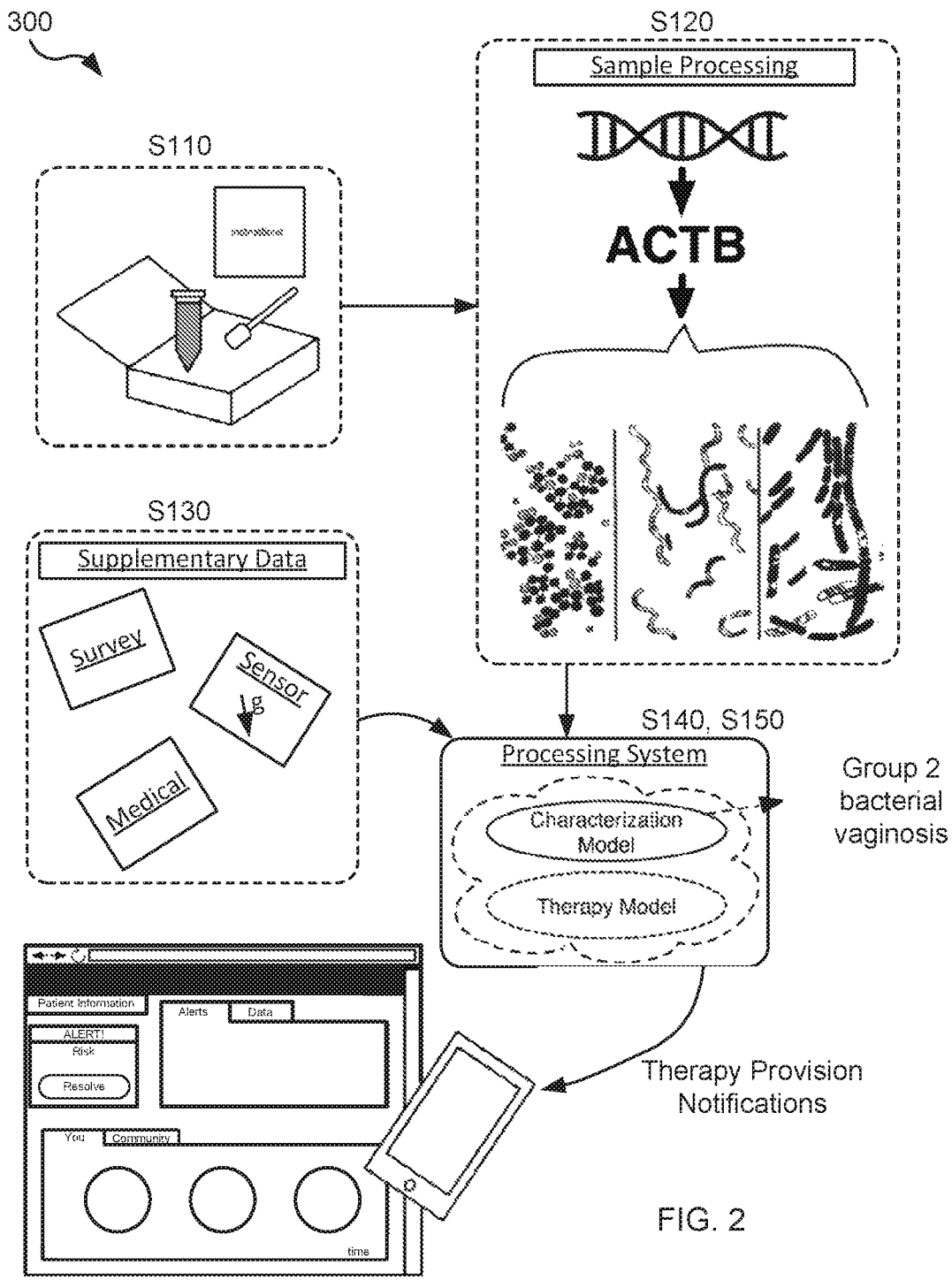
FIG. 2 depicts an embodiment of a method and system for generating microbiome-derived diagnostics and therapeutics.

In one application, at least one of the methods 100, 200 is implemented, at least in part, at a system 300, as shown in FIG. 2, that receives a biological sample derived from the subject (or an environment associated with the subject) by way of a sample reception kit, and processes the biological sample at a processing system implementing a characterization process and a therapy model configured to positively influence a microorganism distribution in the subject (e.g., human, non-human animal, environmental ecosystem, etc.). In variations of the application, the processing system can be configured to generate and/or improve the characterization process and the therapy model based upon sample data received from a population of subjects. The method 100 can, however, alternatively be implemented using any other suitable system(s) configured to receive and process microbiome-related data of subjects, in aggregation with other information, in order to generate models for microbiome-derived diagnostics and associated therapeutics. Thus, the method 100 can be implemented for a population of subjects (e.g., including the subject, excluding the subject), wherein the population of subjects can include patients dissimilar to and/or similar to the subject (e.g., in health condition, in dietary needs, in demographic features, etc.). Thus, information derived from the population of subjects can be used to provide additional insight into connections between behaviors of a subject and effects on the subject's microbiome, due to aggregation of data from a population of subjects.

Thus, the methods 100, 200 can be implemented for a population of subjects (e.g., including the subject, excluding the subject), wherein the population of subjects can include subjects dissimilar to and/or similar to the subject (e.g., health condition, in dietary needs, in demographic features, etc.). Thus, information derived from the population of subjects can be used to provide additional insight into connections between behaviors of a subject and effects on the subject's microbiome, due to aggregation of data from a population of subjects.

A. Sample Handling

Block S110 recites: receiving an aggregate set of biological samples from a population of subjects, which functions to enable generation of data from which models for characterizing subjects and/or providing therapeutic measures to subjects can be generated. In Block S110, biological samples are preferably received from subjects of the population of subjects in a non-invasive manner. In variations, non-invasive manners of sample reception can use any one or more of: a permeable substrate (e.g., a swab configured to wipe a region of a subject's body, toilet paper, a sponge, etc.), a non-permeable substrate (e.g., a slide, tape, etc.), a container (e.g., vial, tube, bag, etc.) configured to receive a sample from a region of a subject's body, and any other suitable sample-reception element. In a specific example, samples can be collected from one or more of a subject's nose, skin, genitals, mouth, and gut in a non-invasive manner (e.g., using a swab and a vial). However, one or more biological samples of the set of biological samples can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can comprise blood samples, plasma/serum samples (e.g., to enable extraction of cell-free DNA), cerebrospinal fluid, and tissue samples. In some cases, the sample is a stool sample, or a sample (e.g., a nucleic acid sample, such as a DNA sample) extracted from a stool sample.

In the above variations and examples, samples can be taken from the bodies of subjects without facilitation by another entity (e.g., a caretaker associated with an individual, a health care professional, an automated or semi-automated sample collection apparatus, etc.), or can alternatively be taken from bodies of individuals with the assistance of another entity. In one example, wherein samples are taken from the bodies of subjects without facilitation by another entity in the sample extraction process, a sample-provision kit can be provided to a subject. In the example, the kit can include one or more swabs or sample vials for sample acquisition, one or more containers configured to receive the swab(s) or sample vials for storage, instructions for sample provision and setup of a user account, elements configured to associate the sample(s) with the subject (e.g., barcode identifiers, tags, etc.), and a receptacle that allows the sample(s) from the individual to be delivered to a sample processing operation (e.g., by a mail delivery system). In another example, wherein samples are extracted from the user with the help of another entity, one or more samples can be collected in a clinical or research setting from a subject (e.g., during a clinical appointment).

In Block S110, the aggregate set of biological samples is preferably received from a wide variety of subjects, and can involve samples from human subjects and/or non-human subjects. In relation to human subjects, Block S110 can include receiving samples from a wide variety of human subjects, collectively including subjects of one or more of: different demographics (e.g., genders, ages, marital statuses, ethnicities, nationalities, socioeconomic statuses, sexual orientations, etc.), different health conditions (e.g., health and disease states), different living situations (e.g., living alone, living with pets, living with a significant other, living with children, etc.), different dietary habits (e.g., omnivorous, vegetarian, vegan, sugar consumption, acid consumption, etc.), different behavioral tendencies (e.g., levels of physical activity, drug use, alcohol use, etc.), different levels of mobility (e.g., related to distance traveled within a given time period), biomarker states (e.g., cholesterol levels, lipid levels, etc.), weight, height, body mass index, genotypic factors, and any other suitable trait that has an effect on microbiome composition. As such, as the number of subjects increases, the predictive power of feature-based models generated in subsequent blocks of the method 100 increases, in relation to characterizing a variety of subjects based upon their microbiomes. Additionally or alternatively, the aggregate set of biological samples received in Block S110 can include receiving biological samples from a targeted group of similar subjects in one or more of: demographic traits, health conditions, living situations, dietary habits, behavior tendencies, levels of mobility, age range (e.g., pediatric, adulthood, geriatric), and any other suitable trait that has an effect on microbiome composition. Additionally or alternatively, the methods 100, and/or 200 can be adapted to characterize diseases typically detected by way of lab tests (e.g., polymerase chain reaction based tests, cell culture based tests, blood tests, biopsies, chemical tests, etc.), physical detection methods (e.g., manometry), medical history based assessments, behavioral assessments, and imagenology based assessments. Additionally or alternatively, the methods 100, 200 can be adapted to characterization of acute conditions, chronic conditions, conditions with difference in prevalence for different demographics, conditions having characteristic disease areas (e.g., the head, the gut, endocrine system diseases, the heart, nervous system diseases, respiratory diseases, immune system diseases, circulatory system diseases, renal system diseases, locomotor system diseases, etc.), and comorbid conditions.

In some embodiments, receiving the aggregate set of biological samples in Block S110 can be performed according to embodiments, variations, and examples of sample reception as described in U.S. application Ser. No. 14/593, 424 filed on 9 Jan. 2015 and entitled "Method and System for Microbiome Analysis", which is incorporated herein in its entirety by this reference. However, receiving the aggregate set of biological samples in Block S110 can additionally or alternatively be performed in any other suitable manner. Furthermore, some alternative variations of the first method 100 can omit Block S110, with processing of data derived from a set of biological samples performed as described below in subsequent blocks of the method 100.

B. Sample Analysis

Block S120 recites: characterizing a microbiome composition and/or functional features for each of the aggregate set of biological samples associated with a population of subjects, thereby generating at least one of a microbiome composition dataset and a microbiome functional diversity dataset for the population of subjects. Block S120 functions to process each of the aggregate set of biological samples, in order to determine compositional and/or functional aspects associated with the microbiome of each of a population of subjects. Compositional and functional aspects can include compositional aspects at the microorganism level, including parameters related to distribution of microorganisms across different groups of kingdoms, phyla, classes, orders, families, genera, species, subspecies, strains, infraspecies taxon (e.g., as measured in total abundance of each group, relative abundance of each group, total number of groups represented, etc.), and/or any other suitable taxa. Compositional and functional aspects can also be represented in terms of operational taxonomic units (OTUs). Compositional and functional aspects can additionally or alternatively include compositional aspects at the genetic level (e.g., regions determined by multilocus sequence typing, 16S sequences, 18S sequences, ITS sequences, other genetic markers, other phylogenetic markers, etc.). Compositional and functional aspects can include the presence or absence or the quantity of genes associated with specific functions (e.g., enzyme activities, transport functions, immune activities, etc.). Outputs of Block S120 can thus be used to provide features of interest for the characterization process of Block S140, wherein the features can be microorganism-based (e.g., presence of a genus of bacteria), genetic-based (e.g., based upon representation of specific genetic regions and/or sequences) and/or functional-based (e.g., presence of a specific catalytic activity, presence of metabolic pathways, etc.).

In one variation, Block S120 can include characterization of features based upon identification of phylogenetic markers derived from bacteria and/or archaea in relation to gene families associated with one or more of: ribosomal protein S2, ribosomal protein S3, ribosomal protein S5, ribosomal protein S7, ribosomal protein S8, ribosomal protein S9, ribosomal protein S10, ribosomal protein S11, ribosomal protein S12/S23, ribosomal protein S13, ribosomal protein S15P/S13e, ribosomal protein S17, ribosomal protein S19, ribosomal protein L1, ribosomal protein L2, ribosomal protein L3, ribosomal protein L4/L1e, ribosomal protein L5, ribosomal protein L6, ribosomal protein L10, ribosomal protein L11, ribosomal protein L1.3, ribosomal protein L14b/L23e, ribosomal protein L15, ribosomal protein L16/L10E, ribosomal protein L18P/L5E, ribosomal protein L22, ribosomal protein L24, ribosomal protein L25/L23, ribosomal protein L29, translation elongation factor EF-2, translation initiation factor IF-2, metalloendopeptidase, ffh signal recognition particle protein, phenylalanyl-tRNA synthetase alpha subunit, phenylalanyl-tRNA synthetase beta subunit, tRNA pseudouridine synthase B, porphobilinogen deaminase, phosphoribosylformylglycinamidine cyclo-ligase, and ribonuclease HII. However, the markers can include any other suitable marker(s).

Characterizing the microbiome composition and/or functional features for each of the aggregate set of biological samples in Block S120 thus can include a combination of sample processing techniques (e.g., wet laboratory techniques) and computational techniques (e.g., utilizing tools of bioinformatics) to quantitatively and/or qualitatively characterize the microbiome and functional features associated with each biological sample from a subject or population of subjects.

In variations, sample processing in Block S120 can include any one or more of: lysing a biological sample, disrupting membranes in cells of a biological sample, separation of undesired elements (e.g., RNA, proteins) from the biological sample, purification of nucleic acids (e.g., DNA) in a biological sample, amplification of nucleic acids from the biological sample, further purification of amplified nucleic acids of the biological sample, and sequencing of amplified nucleic acids of the biological sample. Thus, portions of Block S120 can be implemented using embodiments, variations, and examples of the sample handling network and/or computing system as described in U.S. application Ser. No. 14/593,424 filed on 9 Jan. 2015 and entitled "Method and System for microbiome Analysis", which is incorporated herein in its entirety by this reference. Thus the computing system implementing one or more portions of the method 100 can be implemented in one or more computing systems, wherein the computing system(s) can be implemented at least in part in the cloud and/or as a machine (e.g., computing machine, server, mobile computing device, etc.) configured to receive a computer-readable medium storing computer-readable instructions. However, Block S120 can be performed using any other suitable system(s).

In variations, lysing a biological sample and/or disrupting membranes in cells of a biological sample preferably includes physical methods (e.g., bead beating, nitrogen decompression, homogenization, sonication), which omit certain reagents that produce bias in representation of certain bacterial groups upon sequencing, Additionally or alternatively, lysing or disrupting in Block S120 can involve chemical methods (e.g., using a detergent, using a solvent, using a surfactant, etc.), Additionally or alternatively, lysing or disrupting in Block S120 can involve biological methods. In variations, separation of undesired elements can include removal of RNA using RNases and/or removal of proteins using proteases. In variations, purification of nucleic acids can include one or more of: precipitation of nucleic acids from the biological samples (e.g., using alcohol-based precipitation methods), liquid-liquid based purification techniques (e.g., phenol-chloroform extraction), chromatography-based purification techniques (e.g., column adsorption), purification techniques involving use of binding moiety-bound particles (e.g., magnetic beads, buoyant beads, beads with size distributions, ultrasonically responsive beads, etc.) configured to bind nucleic acids and configured to release nucleic acids in the presence of an elution environment (e.g., having an elution solution, providing a pH shift, providing a temperature shift, etc.), and any other suitable purification techniques.

In variations, performing an amplification operation S123 on purified nucleic acids can include performing one or more of: polymerase chain reaction (PCR)-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and any other suitable amplification technique. In amplification of purified nucleic acids, the primers used are preferably selected to prevent or minimize amplification bias, as well as configured to amplify nucleic acid regions/sequences (e.g., of the 16S region, the 18S region, the ITS region, etc.) that are informative taxonomically, phylogenetically, for diagnostics, for formulations (e.g., for probiotic formulations), and/or for any other suitable purpose. Thus, universal primers (e.g., a F27-R338 primer set for 16S rRNA, a F515-R806 primer set for 16S rRNA, etc. configured to avoid amplification bias can be used in amplification. Primers used in variations of Block S120 (e.g., S123 and/or S124) can additionally or alternatively include incorporated barcode sequences specific to each biological sample, which can facilitate identification of biological samples post-amplification. Primers used in variations of Block S120 (e.g., S123 and/or S124) can additionally or alternatively include adaptor regions configured to cooperate with sequencing techniques involving complementary adaptors (e.g., according to protocols for Illumina Sequencing).

Identification of a primer set for a multiplexed amplification operation can be performed according to embodiments, variations, and examples of methods described in U.S. App. No. 62/206,654 filed 18 Aug. 2015 and entitled "Method and System for Multiplex Primer Design", which is herein incorporated in its entirety by this reference. Performing a multiplexed amplification operation using a set of primers in Block S123 can additionally or alternatively be performed in any other suitable manner.

Figure 3:
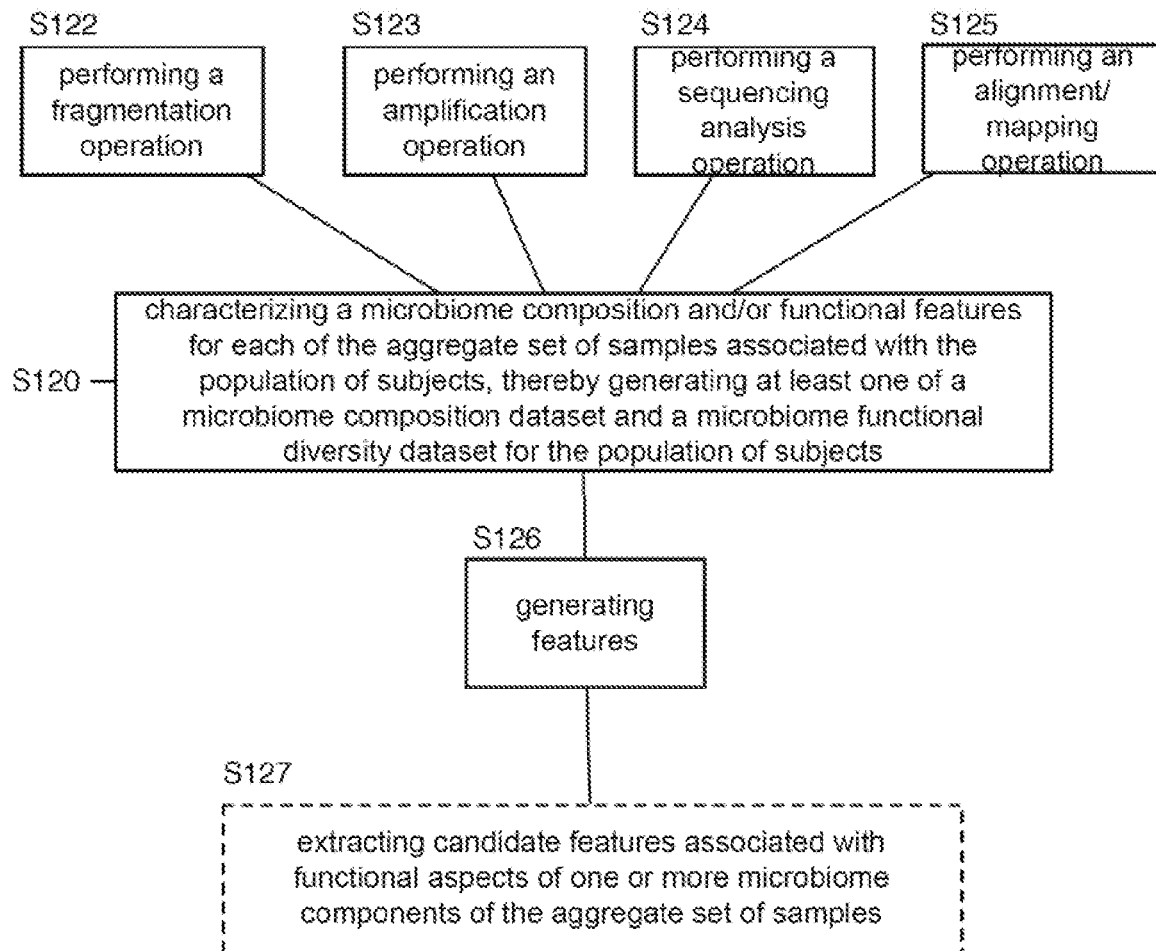
FIG. 3 depicts variations of a portion of an embodiment of a method for generating microbiome-derived diagnostics and therapeutics.

Additionally or alternatively, as shown in FIG. 3, Block S120 can implement any other step configured to facilitate processing (e.g., using a Nextera kit) for performance of a fragmentation operation S122 (e.g., fragmentation and tagging with sequencing adaptors) cooperation with the amplification operation S123 (e.g., S122 can be performed after S123, S122 can be performed before S123, S122 can be performed substantially contemporaneously with S123, etc.). Furthermore, Blocks S122 and/or S123 can be performed with or without a nucleic acid extraction step. For instance, extraction can be performed prior to amplification of nucleic acids, followed by fragmentation, and then amplification of fragments. Alternatively, extraction can be performed, followed by fragmentation and then amplification of fragments. As such, in some embodiments, performing an amplification operation in Block S123 can be performed according to embodiments, variations, and examples of amplification as described in U.S. application Ser. No. 14/593,424 filed on 9 Jan. 2015 and entitled "Method and System for microbiome Analysis". Furthermore, amplification in Block S123 can additionally or alternatively be performed in any other suitable manner.

In a specific example, amplification and sequencing of nucleic acids from biological samples of the set of biological samples includes: solid-phase PCR involving bridge amplification of DNA fragments of the biological samples on a substrate with oligo adapters, wherein amplification involves primers having a forward index sequence (e.g., corresponding to an illumina forward index for miSeq/NextSeq/HiSeq platforms) and/or a reverse index sequence (e.g., corresponding to an Illumina reverse index for MiSeq/NextSeq/HiSeq platforms), a forward barcode sequence and/or a reverse barcode sequence, optionally a transposase sequence (e.g., corresponding to a transposase binding site for MiSeq/NextSeq/HiSeq platforms), optionally a linker (e.g., a zero, one, or two-base fragment configured to reduce homogeneity and improve sequence results), optionally an additional random base, and optionally a sequence for targeting a specific target region (e.g., 16S region, 18S region, ITS region). In some cases, amplification involves one or both primers having any combination of the foregoing elements, or all of the foregoing elements. Amplification and sequencing can further be performed on any suitable amplicon, as indicated throughout the disclosure. In the specific example, sequencing comprises Illumina sequencing (e.g., with a HiSeq platform, with a MiSeq platform, with a NextSeq platform, etc.) using a sequencing-by-synthesis technique. Additionally or alternatively, any other suitable next generation sequencing technology (e.g., PacBio platform, MinION platform, Oxford Nanopore platform, etc.) can be used. Additionally or alternatively, any other suitable sequencing platform or method can be used (e.g., a Roche 454 Life Sciences platform, a Life Technologies SOLiD platform, etc.). In examples, sequencing can include deep sequencing to quantify the number of copies of a particular sequence in a sample and then also be used to determine the relative abundance of different sequences in a sample. The sequencing depth can be, or be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 70, 80, 90, 100, 110, 120, 130, 150, 200, 300, 500, 500, 700, 1000, 2000, 3000, 4000, 5000 or more.

Some variations of sample processing in Block S120 can include further purification of amplified nucleic acids (e.g., PCR products) prior to sequencing, which functions to remove excess amplification elements e.g., primers, dNTPs, enzymes, salts, etc.). In examples, additional purification can be facilitated using any one or more of: purification kits, buffers, alcohols, pH indicators, chaotropic salts, nucleic acid binding filters, centrifugation, and any other suitable purification technique.

In variations, computational processing in Block S120 can include any one or more of: performing a sequencing analysis operation S124 including identification of microbiome-derived sequences (e.g., as opposed to subject sequences and contaminants), performing an alignment and/or mapping operation S125 of microbiome-derived sequences (e.g., alignment of fragmented sequences using one or more of single-ended alignment, ungapped alignment, gapped alignment, pairing), and generating features S126 derived from compositional and/or functional aspects of the microbiome associated with a biological sample.

Performing the sequencing analysis operation S124 with identification of microbiome-derived sequences can include mapping of sequence data from sample processing to a subject reference genome (e.g., provided by the Genome Reference Consortium), in order to remove subject genome-derived sequences. Unidentified sequences remaining after mapping of sequence data to the subject reference genome can then be further clustered into operational taxonomic units (OTUs) based upon sequence similarity and/or reference-based approaches (e.g., using VAMPS, using MG-RAST, and/or using QIIME databases), aligned (e.g., using a genome hashing approach, using a Needleman-Wunsch algorithm, using a Smith-Waterman algorithm); and mapped to reference bacterial genomes (e.g., provided by the National Center for Biotechnology Information), using an alignment algorithm (e.g., Basic Local Alignment Search Tool, FPGA accelerated alignment tool, BWT-indexing with BWA, BWT-indexing with SOAP, BWT-indexing with Bowtie, etc.). Mapping of unidentified sequences can additionally or alternatively include mapping to reference archaeal genomes, viral genomes and/or eukaryotic genomes. Furthermore, mapping of taxa can be performed in relation to existing databases, and/or in relation to custom-generated databases.

Additionally or alternatively, in relation to generating a microbiome functional diversity dataset, Block S120 can include extracting candidate features associated with functional aspects of one or more microbiome components of the aggregate set of biological samples S127, as indicated in the microbiome composition dataset. Extracting candidate functional features can include identifying functional features associated with one or more of: prokaryotic clusters of orthologous groups of proteins (COGs); eukaryotic clusters of orthologous groups of proteins (KOGs); any other suitable type of gene product; an RNA processing and modification functional classification; a chromatin structure and dynamics functional classification; an energy production and conversion functional classification; a cell cycle control and mitosis functional classification; an amino acid metabolism and transport functional classification; a nucleotide metabolism and transport functional classification; a carbohydrate metabolism and transport functional classification; a coenzyme metabolism functional classification; a lipid metabolism functional classification; a translation functional classification; a transcription functional classification; a replication and repair functional classification; a cell wall/membrane/envelop biogenesis functional classification; a cell motility functional classification; a post-translational modification, protein turnover, and chaperone functions functional classification; an inorganic ion transport and metabolism functional classification; a secondary metabolites biosynthesis, transport and catabolism functional classification; a signal transduction functional classification; an intracellular trafficking and secretion functional classification; a nuclear structure functional classification; a cytoskeleton functional classification; a general functional prediction only functional classification; and a function unknown functional classification; and any other suitable functional classification.

Additionally or alternatively, extracting candidate functional features in Block S127 can include identifying functional features associated with one or more of: systems information (e.g., pathway maps for cellular and organismal functions, modules or functional units of genes, hierarchical classifications of biological entities); genomic information (e.g., complete genomes, genes and proteins in the complete genomes, orthologous groups of genes in the complete genomes); chemical information (e.g., chemical compounds and glycans, chemical reactions, enzyme nomenclature); health information (e.g., human diseases, approved drugs, crude drugs and health-related substances); metabolism pathway maps; genetic information processing (e.g., transcription, translation, replication and repair, etc.) pathway maps; environmental information processing (e.g., membrane transport, signal transduction, etc.) pathway maps; cellular processes (e.g., cell growth, cell death, cell membrane functions, etc.) pathway maps; organismal systems (e.g., immune system, endocrine system, nervous system, etc.) pathway maps; human disease pathway maps; drug development pathway maps; and any other suitable pathway map.

In extracting candidate functional features, Block S127 can comprise performing a search of one or more databases, such as the Kyoto Encyclopedia of Genes and Genomes (KEGG) and/or the Clusters of Orthologous Groups (COGs) database managed by the National Center for Biotechnology Information (NCBI). Searching can be performed based upon results of generation of the microbiome composition dataset from one or more of the set of aggregate biological samples and/or sequencing of material from the set of samples. In more detail, Block S127 can include implementation of a data-oriented entry point to a KEGG database including one or more of a KEGG pathway tool, a KEGG BRITE tool, a KEGG module tool, a KEGG ORTHOLOGY (KO) tool, a KEGG genome tool, a KEGG genes tool, a KEGG compound tool, a KEGG glycan tool, a KEGG reaction tool, a KEGG disease tool, a KEGG drug tool, or a G medicus tool. Searching can additionally or alternatively be performed according to any other suitable filters. Additionally or alternatively, Block S127 can include implementation of an organism-specific entry point to a KEGG database including a KEGG organisms tool. Additionally or alternatively, Block S127 can include implementation of an analysis tool including one or more of: a KEGG mapper tool that maps KEGG pathway, BRITE, or module data; a KEGG atlas tool for exploring KEGG global maps, a BlastKOALA tool for genome annotation and KEGG mapping, a BLAST/FASTA sequence similarity search tool, a SIMCOMP chemical structure similarity search tool, and a SUBCOMP chemical substructure search tool. In specific examples, Block S127 can include extracting candidate functional features, based on the microbiome composition dataset, from a KEGG database resource and a COG database resource; moreover, Block S127 can comprise extracting candidate functional features in any other suitable manner. For instance, Block S127 can include extracting candidate functional features, including functional features derived from a Gene Ontology functional classification, and/or any other suitable features.

In one example, a taxonomic group can include one or more bacteria and their corresponding reference sequences. A sequence read can be assigned based on the alignment to a taxonomic group when the sequence read aligns to a reference sequence of the taxonomic group. A functional group can correspond to one or more genes labeled as having a similar function. Thus, a functional group can be represented by reference sequences of the genes in the functional group, where the reference sequences of a particular gene can correspond to various bacteria. The taxonomic and functional groups can collectively be referred to as sequence groups, as each group includes one or more reference sequences that represent the group. A taxonomic group of multiple bacteria can be represented by multiple reference sequence, e.g., one reference sequence per bacteria species in the taxonomic group. Embodiments can use the degree of alignment of a sequence read to multiple reference sequences to determine which sequence group to assign the sequence read based on the alignment.

1. Analysis of Sequence Groups

Instead of or in addition to determining a count of the sequence reads that correspond to a particular taxonomic group, embodiments can use a count of a number of sequence reads that correspond to a particular gene or a collection of genes having an annotation of a particular function, where the collection is called a functional group. The RAV can be determined in a similar manner as for a taxonomic group. For example, functional group can include a plurality of reference sequences corresponding to one or more genes of the functional group. Reference sequences of multiple bacteria for a same gene can correspond to a same functional group. Then, to determine the RAV, the number of sequence reads assigned to the functional group can be used to determine a proportion for the functional group. In exemplary embodiment, the functional group is a KEGG or COG group.

The use of a functional group, which may include a single gene, can help to identify situations where there is a small change (e.g., increase) in many taxonomic groups such that the individual changes are too small to be statistically significant. In such cases, the changes may all be for a same gene or set of genes of a same functional group, and thus the change for that functional group can be statistically significant, even though the changes for the taxonomic groups may not be statistically significant for a given sequence dataset. The reverse can be true of a taxonomic group being more predictive than a particular functional group, e.g., when a single taxonomic group includes many genes that have changed by a relatively small amount.

As an example, if 10 taxonomic groups increase by approximately 10%, the statistical power to discriminate between the two groups may be low when each taxonomic group is analyzed individually. But, if the increase is similar all for genes(s) of a shared functional group, then the increase would be 100%, or a doubling of the proportion for that taxonomic group. This large increase would have a much larger statistical power for discriminating between the two groups. Thus, the functional group can act to provide a sum of small changes for various taxonomic groups. And, small changes for various functional groups, which happen to all be on a same taxonomic group, can sum to provide high statistical power for that particular taxonomic group.

2, Exemplary Pipeline for Detecting and Analyzing Taxonomic Groups

Embodiments can provide a bioinformatics pipeline that taxonomically annotates the microorganisms present in a sample. The example clinical annotation pipeline can comprise the following procedures described herein. FIG. 1C is a flowchart of an embodiment of a method for estimating the relative abundances of a plurality of taxa from a sample and outputting the estimates to a database.

In block 30, the samples can be identified and the sequence data can be loaded. For example, the pipeline can begin with demultiplexed fastq files (or other suitable files) that are the product of pair-end sequencing of amplicons (e.g., of the V4 region of the 16S gene). All samples can be identified for a given input sequencing file, and the corresponding fastq files can be obtained from the fastq repository server and loaded into the pipeline.

In block 31, the reads can be filtered. For example, a global quality filtering of reads in the fastq files can accept reads with a global Q-score >30, In one implementation, for each read, the per-position Q-scores are averaged, and if the average is equal or higher than 30, then the read is accepted, else the read is discarded, as is its paired read.

In block 32, primers can be identified and removed. In one embodiment, only forward reads that contain the forward primer and reverse reads that contain the reverse primer (allowing annealing of printers with up to 5 mismatches or other number of mismatches) are further considered. Primers and any sequences 5' to them are removed from the reads. The 125 bp (or other suitable number) towards the 3' of the forward primer are considered from the forward reads, and only 124 bp (or other suitable number) towards the 3' of the reverse primer are considered for the reverse reads. All processed forward reads that are <125 bp and reverse reads that are <124 bp are eliminated from further processing as are their paired reads.

In block 33, the forward and reverse reads can be written to files (e.g., FASTA files). For example, the forward and reverse reads that remained paired can be used to generate files that contain 125 bp from the forward read, concatenated to 124 bp from the reverse read (in the reverse complement direction).

In block 34, the sequence reads can be clustered, e.g., to identify chimeric sequences or determine a consensus sequence for a bacterium. For example, the sequences in the files can be subjected to clustering using the Swarm algorithm [Mahé, F. et al. 2014] with a distance of 1. This treatment allows the generation of cluster composed of a central biological entity, surrounded by sequences which are 1 mutation away from the biological entity, which are less abundant and the result of the normal base calling error associated to high throughput sequencing. Singletons are removed from further analyses. In the remaining clusters, the most abundant sequence per cluster is then used as the representative and assigned the counts of all members in the cluster.

In block 35, chimeric sequences can be removed. For example, amplification of gene superfamilies can produce the formation of chimeric DNA sequences. These result from a partial PCR product from one member of the superfamily that anneals and extends over a different member of the superfamily in a subsequent cycle of PCR. In order to remove chimeric DNA sequences, some embodiments can use the VSEARCH chimera detection algorithm with the de novo option and standard parameters [Rognes, T. et al. 2016]. This algorithm uses abundance of PCR products to identify reference "real" sequences as those most abundant, and chimeric products as those less abundant and displaying local similarity to two or more of the reference sequences. All chimeric sequences can be removed from further analysis.

In block 36, taxonomy annotation can be assigned to sequences using sequence identity searches. To assign taxonomy to the sequences that have passed all filters above, some embodiments can perform identity searches against a database that contains bacterial strains (e.g., reference sequences) annotated to phylum, class, order, family, genus and species level, at least to a subsection of those taxonomic levels, or any other taxonomic levels. The most specific level of taxonomic annotation for a sequence can be kept, given that higher order taxonomy designations for a lower level taxonomy level can be inferred. The sequence identity search can be performed using the algorithm VSEARCH [Rognes, T. et al. 2016] with parameters (maxaccepts=0, maxrejects=0, id=1) that allow an exhaustive exploration of the reference database used. Decreasing values of sequence identity can be used to assign sequences to different taxonomic groups: >97% sequence identity for assigning to a species, >95% sequence identity for assigning to a genus, >90% for assigning to family, >85% for assigning to order, >80% for assigning to class, and >77% for assigning to phylum.

In block 37, relative abundances of each taxa can be estimated and output to a database. For example, once all sequences have been used to identify identical sequences in the reference database, relative abundance per taxa can be determined by dividing the count of all sequences that are assigned to the same taxonomic group by the total number of reads that passed filters, e.g., were assigned. Results can be uploaded to database tables that are used as repository for the taxonomic annotation data.

3. Exemplary Pipeline for Detecting and Analyzing Functional Groups

For functional groups, the process can proceed as follows. FIG. 1D is a flowchart of an embodiment of a method for generating features derived from composition and/or functional components of a biological sample or an aggregate of biological samples.

In block 40, sample OTUs (Operational Taxonomic Units) can be found. This may occur, e.g., after the sixth block described above in section V.B.2. After sample OTUs are found, sequences can be clustered, e.g., based on sequence identity (e.g., 97% sequence identity).

In block 41, a taxonomy can be assigned, e.g., by comparing OTUs with reference sequences of known taxonomy. The comparison can be based on sequence identity (e.g., 97%).

In block 42, taxonomic abundance can be adjusted for 16S copy number, or whatever genomic regions may be analyzed. Different species may have different number of copies of the 16S gene, so those possessing a higher number of copies will have more 16S material for PCR amplification at same number of cells than other species. Therefore, abundance can be normalized by adjusting the number of 16S copies.

In block 43, a pre-computed genomic lookup table can be used to relate taxonomy to functions, and amount of function. For example, a pre-computed genomic lookup table that shows the number of genes for important KEGG or COG functional categories per taxonomic group can be used to estimate the abundance of those functional categories based on the normalized 16S abundance data.

Upon identification of represented groups of microorganisms of the microbiome associated with a biological sample and/or identification of candidate functional aspects (e.g., functions associated with the microbiome components of the biological samples), generating features derived from compositional and/or functional aspects of the microbiome associated with the aggregate set of biological samples can be performed.

In one variation, generating features can include generating features derived from multilocus sequence typing (MLST), which can be performed experimentally at any stage in relation to implementation of the methods 100, 200, in order to identify markers useful for characterization in subsequent blocks of the method 100. Additionally or alternatively, generating features can include generating features that describe the presence or absence of certain taxonomic groups of microorganisms, and/or ratios between exhibited taxonomic groups of microorganisms. Additionally or alternatively, generating features can include generating features describing one or more of: quantities of represented taxonomic groups, networks of represented taxonomic groups, correlations in representation of different taxonomic groups, interactions between different taxonomic groups, products produced by different taxonomic groups, interactions between products produced by different taxonomic groups, ratios between dead and alive microorganisms (e.g., for different represented taxonomic groups, e.g., based upon analysis of RNAs), phylogenetic distance (e.g., in terms of Kantorovich-Rubinstein distances, Wasserstein distances etc.), any other suitable taxonomic group-related feature(s), or any other suitable genetic or functional feature(s).

Additionally or alternatively, generating features can include generating features describing relative abundance of different microorganism groups, for instance, using a sparCC approach, using Genome Relative Abundance and Average size (GAAS) approach and/or using a genome Relative Abundance using Mixture Model theory (GRAMM) approach that uses sequence-similarity data to perform a maximum likelihood estimation of the relative abundance of one or more groups of microorganisms. Additionally or alternatively, generating features can include generating statistical measures of taxonomic variation, as derived from abundance metrics. Additionally or alternatively, generating features can include generating features derived from relative abundance factors (e.g., in relation to changes in abundance of a taxon, which affects abundance of other taxa). Additionally or alternatively, generating features can include generation of qualitative features describing presence of one or more taxonomic groups, in isolation and/or in combination. Additionally or alternatively, generating features can include generation of features related to genetic markers (e.g., representative 16S, 18S, and/or ITS sequences) characterizing microorganisms of the microbiome associated with a biological sample. Additionally or alternatively, generating features can include generation of features related to functional associations of specific genes and/or organisms having the specific genes. Additionally or alternatively, generating features can include generation of features related to pathogenicity of a taxon and/or products attributed to a taxon. Block S120 can, however, include generation of any other suitable feature(s) derived from sequencing and mapping of nucleic acids of a biological sample. For instance, the feature(s) can be combinatory (e.g., involving pairs, triplets), correlative (e.g., related to correlations between different features), and/or related to changes in features (i.e., temporal changes, changes across sample sites, spatial changes, etc.). Features can, however, be generated in any other suitable manner in Block S120.

4. Use of Supplementary Data

Block S130 recites: receiving a supplementary dataset, associated with at least a subset of the population of subjects, wherein the supplementary dataset is informative of characteristics associated with the disease or condition. The supplementary dataset can thus be informative of presence of the disease within the population of subjects. Block S130 functions to acquire additional data associated with one or more subjects of the set of subjects, which can be used to train and/or validate the characterization processes performed in block S140. In Block S130, the supplementary dataset can include survey-derived data, and can additionally or alternatively include any one or more of: contextual data derived from sensors, medical data (e.g., current and historical medical data associated with a bacterial vaginosis issue or health conditions associated with a bacterial vaginosis issue, behavioral instrument data, data derived from a tool derived from the Diagnostic and Statistical Manual of Mental Disorders, etc.), and any other suitable type of data.

In variations of Block S130 including reception of survey-derived data, the survey-derived data preferably provides physiological, demographic, and behavioral information in association with a subject. Physiological information can include information related to physiological features (e.g., height, weight, body mass index, body fat percent, body hair level, etc.). Demographic information can include information related to demographic features (e.g., gender, age, ethnicity, marital status, number of siblings, socioeconomic status, sexual orientation, etc.). Behavioral information can include information related to one or more of: health conditions (e.g., health and disease states), living situations (e.g., living alone, living with pets, living with a significant other, living with children, etc.), dietary habits (e.g., omnivorous, vegetarian, vegan, sugar consumption, acid consumption, etc.), behavioral tendencies (e.g., levels of physical activity, drug use, alcohol use, etc.), different levels of mobility (e.g., related to distance traveled within a given time period), different levels of sexual activity (e.g., related to numbers of partners and sexual orientation), and any other suitable behavioral information. Survey-derived data can include quantitative data and/or qualitative data that can be converted to quantitative data (e.g., using scales of severity, mapping of qualitative responses to quantified scores, etc.).

In facilitating reception of survey-derived data, Block S130 can include providing one or more surveys to a subject of the population of subjects, or to an entity associated with a subject of the population of subjects. Surveys can be provided in person (e.g., in coordination with sample provision and/or reception from a subject), electronically (e.g., during account setup by a subject, at an application executing at an electronic device of a subject, at a web application accessible through an internet connection, etc.), and/or in any other suitable manner.

Additionally or alternatively, portions of the supplementary dataset received in Block S130 can be derived from sensors associated with the subject(s) (e.g., sensors of wearable computing devices, sensors of mobile devices, biometric sensors associated with the user, etc. As such, Block S130 can include receiving one or more of: physical activity- or physical action-related data (e.g., accelerometer and gyroscope data from a mobile device or wearable electronic device of a subject), environmental data (e.g., temperature data, elevation data, climate data, light parameter data, etc.), patient nutrition or diet-related data (e.g., data from food establishment check-ins, data from spectrophotometric analysis, etc.), biometric data (e.g., data recorded through sensors within the patient's mobile computing device, data recorded through a wearable or other peripheral device in communication with the patient's mobile computing device), location data (e.g., using GPS elements), and any other suitable data. Additionally or alternatively, portions of the supplementary dataset can be derived from medical record data and/or clinical data of the subject(s). As such, portions of the supplementary dataset can be derived from one or more electronic health records (EHRs) of the subject(s).

Additionally or alternatively, the supplementary dataset of Block S130 can include any other suitable diagnostic information (e.g., clinical diagnosis information), which can be combined with analyses derived from features to support characterization of subjects in subsequent blocks of the method 100. For instance, information derived from a colonoscopy, biopsy, blood test, diagnostic imaging, survey-related information, and any other suitable test can be used to supplement Block S130.

5. Characterization of Bacterial Vaginosis Issues

Block S140 recites: transforming the supplementary dataset and features extracted from at least one of the microbiome composition dataset and the microbiome functional diversity dataset into a characterization model of the disease or condition. Block S140 functions to perform a characterization process for identifying features and/or feature combinations that can be used to characterize subjects or groups with a bacterial vaginosis issue based upon their microbiome composition and/or functional features. Additionally or alternatively, the characterization process can be used as a diagnostic tool that can characterize a subject (e.g., in terms of behavioral traits, in terms of medical conditions, in terms of demographic traits, etc.) based upon their microbiome composition and/or functional features, in relation to other health condition states, behavioral traits, medical conditions, demographic traits, and/or any other suitable traits. Such characterization can then be used to suggest or provide personalized therapies by way of the therapy model of Block S150.

In performing the characterization process, Block S140 can use computational methods (e.g., statistical methods, machine learning methods, artificial intelligence methods, bioinformatics methods, etc.) to characterize a subject as exhibiting features characteristic of a group of subjects with a bacterial vaginosis issue.

In one variation, characterization can be based upon features derived from a statistical analysis (e.g., an analysis of probability distributions) of similarities and/or differences between a first group of subjects exhibiting a target state (e.g., a health condition state) associated with the bacterial vaginosis issue, and a second group of subjects not exhibiting the target state (e.g., a "normal" state) associated with absence of a bacterial vaginosis issue, or the absence of a microbiome indicative of a bacterial vaginosis issue, or the absence of a microbiome indicative of a health and/or quality of life issue caused by a bacterial vaginosis issue. In implementing this variation, one or more of a Kolmogorov-Smirnov (KS) test, a permutation test, a Cramér-von Mises test, and any other statistical test (e.g., t-test, Welch's t-test, z-test, chi-squared test, test associated with distributions, etc.) can be used. In particular, one or more such statistical hypothesis tests can be used to assess a set of features having varying degrees of abundance in (or variations across) a first group of subjects exhibiting a target state (e.g., an adverse state) associated with the a bacterial vaginosis issue and a second group of subjects not exhibiting the target state (e.g., having a normal state) associated with the bacterial vaginosis issue. In more detail, the set of features assessed can be constrained based upon percent abundance and/or any other suitable parameter pertaining to diversity in association with the first group of subjects and the second group of subjects, in order to increase or decrease confidence in the characterization. In a specific implementation of this example, a feature can be derived from a taxon of microorganism and/or presence of a functional feature that is abundant in a certain percentage of subjects of the first group and subjects of the second group, wherein a relative abundance of the taxon between the first group of subjects and the second group of subjects can be determined from one or more of a KS test or a Welch's t-test (e.g., a t-test with a log normal transformation), with an indication of significance e.g., in terms of p-value). Thus, an output of Block S140 can comprise a normalized relative abundance value (e.g., 25% greater abundance of a taxon-derived feature and/or a functional feature in bacterial vaginosis issue subjects vs. control subjects) with an indication of significance (e.g., a p-value of 0.0013), Variations of feature generation can additionally or alternatively implement or be derived from functional features or metadata features (e.g., non-bacterial markers).

In variations and examples, characterization can use the relative abundance values (RAVs) for populations of subjects that have the disease (a bacterial vaginosis issue) and that do not have the disease (control population). If the distribution of RAVs of a particular sequence group for the disease population is statistically different than the distribution of RAVs for the control population, then the particular sequence group can be identified for including in a disease signature. Since the two populations have different distributions, the RAV for a new sample for a sequence group in the disease signature can be used to classify (e.g., determine a probability) of whether the sample does or does not have, or is indicative of, the disease. The classification can also be used to determine a treatment, as is described herein. A discrimination level can be used to identify sequence groups that have a high predictive value. Thus, embodiment can filter out taxonomic groups and/or functional groups that are not very accurate for providing a diagnosis.

Once RAVs of a sequence group have been determined for the control and disease populations, various statistical tests can be used to determine the statistical power of the sequence group for discriminating between disease (a bacterial vaginosis issue) and the absence of the disease (control). In one embodiment, the Kolmogorov-Smirnov (KS) test can be used to provide a probability value (p-value) that the two distributions are actually identical. The smaller the p-value the greater the probability to correctly identify which population a sample belongs. The larger the separation in the mean values between the two populations generally results in a smaller p-value (an example of a discrimination level). Other tests for comparing distributions can be used. The Welch's t-test presumes that the distributions are Gaussian, which is not necessarily true for a particular sequence group. The KS test, as it is a non-parametric test, is well suited for comparing distributions of taxa or functions for which the probability distributions are unknown.

The distribution of the RAVs for the control and disease populations can be analyzed to identify sequence groups with a large separation between the two distributions. The separation can be measured as a p-value (See example section). For example, the RAVs for the control population may have a distribution peaked at a first value with a certain width and decay for the distribution. And, the disease population can have another distribution that is peaked a second value that is statistically different than the first value. In such an instance, an abundance value of a control sample has a lower probability to be within the distribution of abundance values encountered for the disease samples. The larger the separation between the two distributions, the more accurate the discrimination is for determining whether a given sample belongs to the control population or the disease population. As is described herein, the distributions can be used to determine a probability for an RAV as being in the control population and determine a probability for the RAV being in the disease population, where sequence groups associated with the largest percentage difference between two means have the smallest p-value, signifying a greater separation between the two populations.

In performing the characterization process, Block S140 can additionally or alternatively transform input data from at least one of the microbiome composition datasets and/or microbiome functional diversity datasets into feature vectors that can be tested for efficacy in predicting characterizations of the population of subjects. Data from the supplementary dataset can be used to inform characterizations of the bacterial vaginosis issue, wherein the characterization process is trained with a training dataset of candidate features and candidate classifications to identify features and/or feature combinations that have high degrees (or low degrees) of predictive power in accurately predicting a classification. As such, refinement of the characterization process with the training dataset identifies feature sets (e.g., of subject features, of combinations of features) having high correlation with a bacterial vaginosis issue or a health issue (e.g., symptom) associated with a bacterial vaginosis issue.

In some embodiments, feature vectors effective in predicting classifications of the characterization process can include features related to one or more of: microbiome diversity metrics (e.g., in relation to distribution across taxonomic groups, in relation to distribution across archaeal, bacterial, viral, and/or eukaryotic groups), presence of taxonomic groups in one's microbiome, representation of specific genetic sequences (e.g., 16S sequences) in one's microbiome, relative abundance of taxonomic groups in one's microbiome, microbiome resilience metrics (e.g., in response to a perturbation determined from the supplementary dataset), abundance of genes that encode proteins or RNAs with given functions (enzymes, transporters, proteins from the immune system, hormones, interference RNAs, etc.) and any other suitable features derived from the microbiome composition dataset, the microbiome functional diversity dataset (e.g., COG-derived features, KEGG derived features, other functional features, etc.), and/or the supplementary dataset. Additionally, combinations of features can be used in a feature vector, wherein features can be grouped and/or weighted in providing a combined feature as part of a feature set. For example, one feature or feature set can include a weighted composite of the number of represented classes of bacteria in one's microbiome, presence of a specific genus of bacteria in one's microbiome, representation of a specific 16S sequence in one's microbiome, and relative abundance of a first phylum over a second phylum of bacteria. However, the feature vectors can additionally or alternatively be determined in any other suitable manner.

In examples of Block S140, assuming sequencing has occurred at a sufficient depth, one can quantify the number of reads for sequences indicative of the presence of a feature, thereby allowing one to set a value for an estimated amount of one of the criteria. The number of reads or other measures of amount of one of the features can be provided as an absolute or relative value. An example of an absolute value is the number of reads of 16S rRNA coding sequence reads that map to the genus of Lacnospira. Alternatively, relative amounts can be determined. An exemplary relative amount calculation is to determine the amount of 16S rRNA coding sequence reads for a particular bacterial taxon (e.g., genus, family, order, class, or phylum) relative to the total number of 16S rRNA coding sequence reads assigned to the bacterial domain. A value indicative of amount of a feature in the sample can then be compared to a cut-off value or a probability distribution in a disease signature for a bacterial vaginosis issue. For example, if the disease signature indicates that a relative amount of feature #1 of 50% or more of all features possible at that level indicates the likelihood of a bacterial vaginosis issue or a health or quality of life issue attributable to, indicative of, or caused by a bacterial vaginosis issue, then quantification of gene sequences associated with feature #1 less than 50% in a sample would indicate a higher likelihood of being from a healthy subject (or at least from a subject that does not have a bacterial vaginosis issue, or does not have a specific bacterial vaginosis issue) and alternatively, quantification of gene sequences associated with feature #1 of more than 50% in a sample would indicate a higher likelihood of the disease.

In some cases, the taxonomic groups and/or functional groups can be referred to as features, or as sequence groups in the context of determining an amount of sequence reads corresponding to a particular group (feature). In some cases, scoring of a particular bacteria or genetic pathway can be determined according to a comparison of an abundance value to one or more reference (calibration) abundance values for known samples, e.g., where a detected abundance value less than a certain value is associated with the a bacterial vaginosis issue in question and above the certain value is scored as associated with healthy, or vice versa depending on the particular criterion. The scoring for various bacteria or genetic pathways can be combined to provide a classification for a subject. Furthermore, in the examples, the comparison of an abundance value to one or more reference abundance values can include a comparison to a cutoff value determined from the one or more reference values. Such cutoff value(s) can be part of a decision tree or a clustering technique (where a cutoff value is used to determine which cluster the abundance value(s) belong) that are determined using the reference abundance values. The comparison can include intermediate determination of other values, (e.g., probability values). The comparison can also include a comparison of an abundance value to a probability distribution of the reference abundance values, and thus a comparison to probability values.

A disease signature can include more sequence groups than are used for a given subject. As an example, the disease signature can include 100 sequence groups, but only 60 of sequence groups may be detected in a sample, or detected above a threshold cutoff. The classification of the subject (including any probability for having or lacking a disease such as a bacterial vaginosis issue) can be determined based on the 60 sequence groups.

In relation to generation of the characterization model, the sequence groups with high discrimination levels (e.g., low p-values) for a given disease can be identified and used as part of a characterization model, e.g., which uses a disease signature to determine a probability of a subject having a bacterial vaginosis issue. The disease signature can include a set of sequence groups as well as discriminating criteria (e.g., cutoff values and/or probability distributions) used to provide a classification of the subject. The classification can be binary (e.g., disease or control) or have more classifications (e.g., probability values for having the disease of a bacterial vaginosis issue, or not having the disease). Which sequence groups of the disease signature that are used in making a classification be dependent on the specific sequence reads obtained, e.g., a sequence group would not be used if no sequence reads were assigned to that sequence group. In some embodiments, a separate characterization model can be determined for different populations, e.g., by geography where the subject is currently residing (e.g., country, region, or continent), the generic history of the subject (e.g., ethnicity), or other factors.

Figure 4:
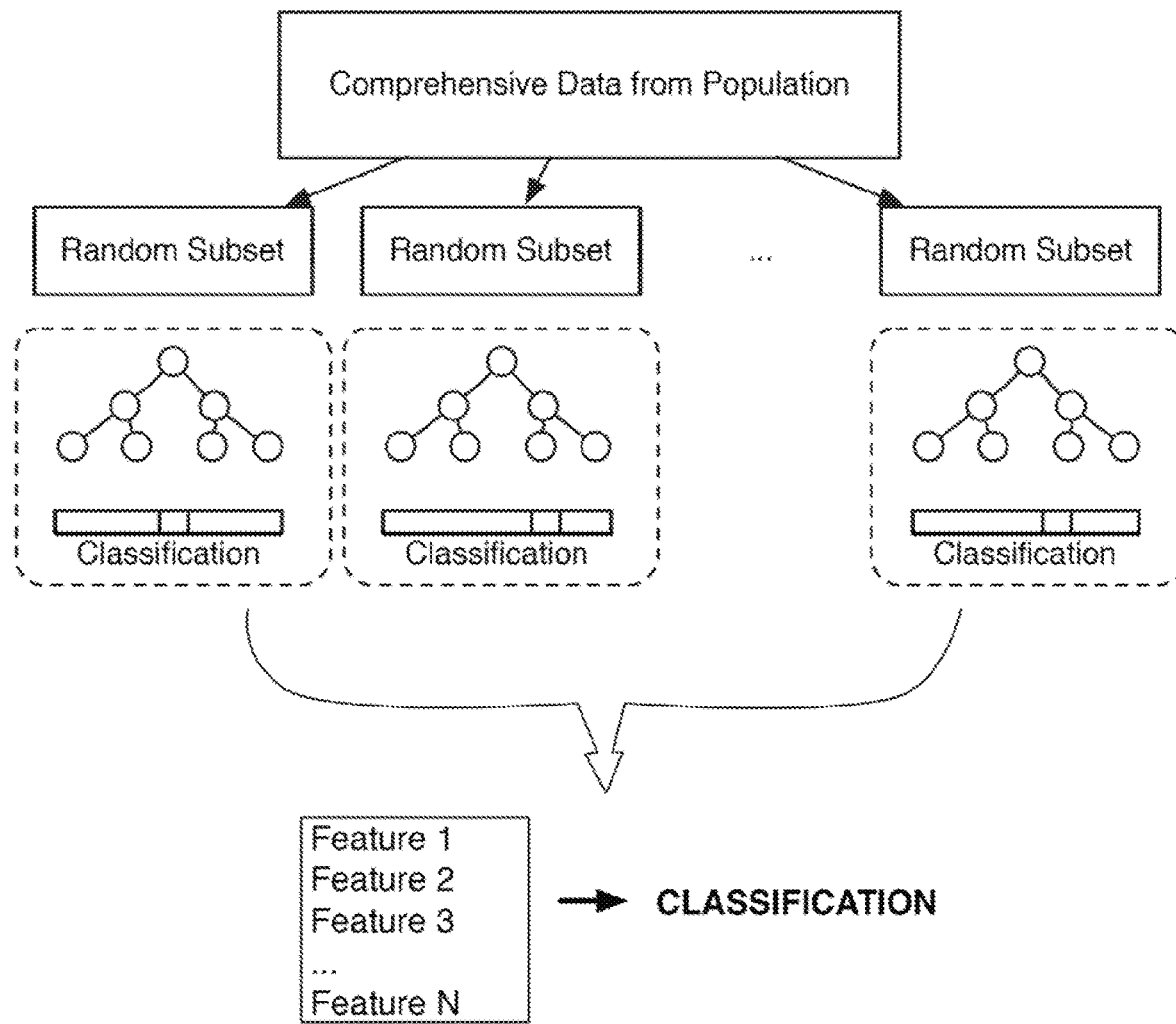
FIG. 4 depicts a variation of a process for generation of a model in an embodiment of a method and system for generating microbiome-derived diagnostics and therapeutics.

6. Selection of Sequence Groups, Discrimination Criteria for Sequence Groups, and Use of Sequence Groups As shown in FIG. 4, in one embodiment of Block S140, the characterization process can be generated and trained according to a random forest predictor (RFP) algorithm that combines bagging (i.e., bootstrap aggregation) and selection of random sets of features from a training dataset to construct a set of decision trees, T, associated with the random sets of features. In using a random forest algorithm, N cases from the set of decision trees are sampled at random with replacement to create a subset of decision trees, and for each node, m prediction features are selected from all of the prediction features for assessment. The prediction feature that provides the best split at the node (e.g., according to an objective function) is used to perform the split (e.g., as a bifurcation at the node, as a trifurcation at the node). By sampling many times from a large dataset, the strength of the characterization process, in identifying features that are strong in predicting classifications can be increased substantially. In this variation, measures to prevent bias (e.g., sampling bias) and/or account for an amount of bias can be included during processing to increase robustness of the model.

In one implementation, a characterization process of Block S140 based upon statistical analyses can identify the sets of features that have the highest correlations with a bacterial vaginosis issue, for which one or more therapies would have a positive effect, based upon an algorithm trained and validated with a validation dataset derived from a subset of the population of subjects. In particular, a bacterial vaginosis issue in this first variation is characterized by an alteration of the microbiome that is predictive of the presence or absence of bacterial vaginosis.

In one variation, a set of features useful for diagnostics associated with bacterial vaginosis includes features derived from one or more of the taxa of Table A (e.g., one or more of the species, genera, families, orders, and/or classes of Table A) and/or one or more of the functional groups of Table A (e.g., one or more of the KEGG level 2 (KEGG L2) functional groups and/or one or more of the KEGG level 3 (KEGG L3) functional groups of Table A).

7. Therapy Models

In some embodiments, as noted above, outputs of the first method 100 can be used to generate diagnostics and/or provide therapeutic measures for an individual based upon an analysis of the individual's microbiome. As such, a second method 200 derived from at least one output of the first method 100 can include: receiving a biological sample from a subject S210; characterizing the subject with a form of a bacterial vaginosis issue based upon the characterization and the therapy model S230.

Block S210 recites: receiving a biological sample from the subject, which functions to facilitate generation of a microbiome composition dataset and/or a microbiome functional diversity dataset for the subject. As such, processing and analyzing the biological sample preferably facilitates generation of a microbiome composition dataset and/or a microbiome functional diversity dataset for the subject, which can be used to provide inputs that can be used to characterize the individual in relation to diagnosis of the bacterial vaginosis issue, as in Block S220. Receiving a biological sample from the subject is preferably performed in a manner similar to that of one of the embodiments, variations, and/or examples of sample reception described in relation to Block S110 above. As such, reception and processing of the biological sample in Block S210 can be performed for the subject using similar processes as those for receiving and processing biological samples used to generate the characterization(s) and/or the therapy provision model of the first method 100, in order to provide consistency of process. However, biological sample reception and processing in Block S210 can alternatively be performed in any other suitable manner.

Block S220 recites: characterizing the subject characterizing the subject with a form of a disease or condition based upon processing a microbiome dataset derived from the biological sample. Block S220 functions to extract features from microbiome-derived data of the subject, and use the features to positively or negatively characterize the individual as having a form of the bacterial vaginosis issue. Characterizing the subject in Block S220 thus preferably includes identifying features and/or combinations of features associated with the microbiome composition and/or functional features of the microbiome of the subject, and comparing such features with features characteristic of subjects with the bacterial vaginosis issue. Block S220 can further include generation of and/or output of a confidence metric associated with the characterization for the individual. For instance, a confidence metric can be derived from the number of features used to generate the classification, relative weights or rankings of features used to generate the characterization, measures of bias in the models used in Block S140 above, and/or any other suitable parameter associated with aspects of the characterization operation of Block S140.

In some variations, features extracted from the microbiome dataset can be supplemented with survey-derived and/or medical history-derived features from the individual, which can be used to further refine the characterization operation(s) of Block S220. However, the microbiome composition dataset and/or the microbiome functional diversity dataset of the individual can additionally or alternatively be used in any other suitable manner to enhance the first method 100 and/or the second method 200.

Block S230 recites: promoting a therapy to the subject with disease or condition based upon the characterization and the therapy model. Block S230 functions to recommend or provide a personalized therapeutic measure to the subject, in order to shift the microbiome composition of the individual toward a desired equilibrium state. As such, Block S230 can include correcting the bacterial vaginosis issue, or otherwise positively affecting the user's health in relation to the bacterial vaginosis issue. Block S230 can thus include promoting one or more therapeutic measures to the subject based upon their characterization in relation to the bacterial vaginosis issue, as described herein, wherein the therapy is configured to modulate taxonomic makeup of the subject's microbiome and/or modulate functional feature aspects of the subject in a desired manner toward a "normal" or "control" state in relation to the characterizations described above.

In Block S230, providing the therapeutic measure to the subject can include recommendation of available therapeutic measures configured to modulate microbiome composition of the subject toward a desired state (e.g., having a microbiome that is not indicative of (e.g., altered by) a bacterial vaginosis issue). Additionally or alternatively, Block S230 can include provision of customized therapy to the subject according to their characterization (e.g., in relation to a specific type of bacterial vaginosis issue). In variations, therapeutic measures for adjusting a microbiome composition of the subject, in order to improve a state of the bacterial vaginosis issue can include one or more of: probiotics, prebiotics, bacteriophage-based therapies, consumables, suggested activities, topical therapies, adjustments to hygienic product usage, adjustments to diet, adjustments to sleep behavior, living arrangement, adjustments to level of sexual activity, nutritional supplements, medications, antibiotics, and any other suitable therapeutic measure. Therapy provision in Block S230 can include provision of notifications by way of an electronic device, through an entity associated with the individual, and/or in any other suitable manner.

Figure 6:
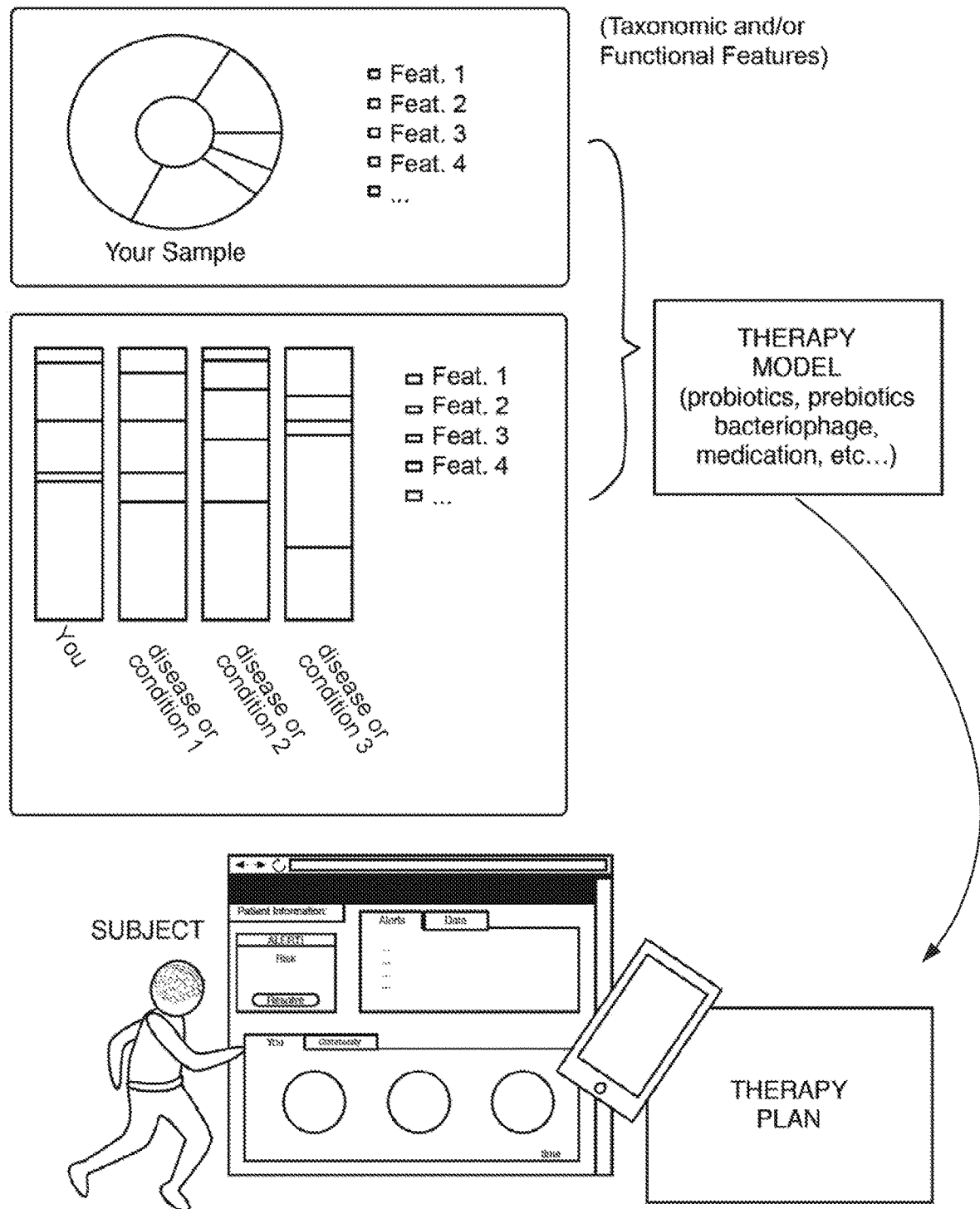
FIG. 6 depicts examples of therapy-related notification provision in an example of a method for generating microbiome-derived diagnostics and therapeutics.

In more detail, therapy provision in Block S230 can include provision of notifications to the subject regarding recommended therapeutic measures and/or other courses of action, in relation to health-related goals, as shown in FIG. 6. Notifications can be provided to an individual by way of an electronic device (e.g., personal computer, mobile device, tablet, head-mounted wearable computing device, wrist-mounted wearable computing device, etc.) that executes an application, web interface, and/or messaging client configured for notification provision. In one example, a web interface of a personal computer or laptop associated with a subject can provide access, by the subject, to a user account of the subject, wherein the user account includes information regarding the subject's characterization, detailed characterization of aspects of the subject's microbiome composition and/or functional features, and notifications regarding suggested therapeutic measures generated in Block S150. In another example, an application executing at a personal electronic device (e.g., smart phone, smart watch, head-mounted smart device) can be configured to provide notifications (e.g., at a display, haptically, in an auditory manner, etc.) regarding therapeutic suggestions generated by the therapy model of Block S150. Notifications can additionally or alternatively be provided directly through an entity associated with a subject (e.g., a caretaker, a spouse, a significant other, a healthcare professional, etc.). In some further variations, notifications can additionally or alternatively be provided to an entity (e.g., healthcare professional) associated with the subject, wherein the entity is able to administer the therapeutic measure (e.g., by way of prescription, by way of conducting a therapeutic session, etc.), Notifications can, however, be provided for therapy administration to the subject in any other suitable manner.

Furthermore, in an extension of Block S230, monitoring of the subject during the course of a therapeutic regimen (e.g., by receiving and analyzing biological samples from the subject throughout therapy, by receiving survey-derived data from the subject throughout therapy) can be used to generate a therapy-effectiveness model for each recommended therapeutic measure provided according to the model generated in Block S150.

As shown in FIG. 1E, in some variations, the first method 100, or any of the methods described herein (e.g., as in any one or more of FIGS. 1A-1F) can further include Block S150, which recites: based upon the characterization model, generating a therapy, model configured to correct or otherwise improve a state of the disease or condition. Block S150 functions to identify or predict therapies (e.g., probiotic-based therapies, prebiotic-based therapies, phage-based therapies, small molecule-based therapies (e.g., selective, pan-selective, or non-selective antibiotics), etc.) that can shift a subject's microbiome composition and/or functional features toward a desired equilibrium state in promotion of the subject's health (e.g., toward a microbiome that is not altered by the bacterial vaginosis issue that occurred prior to the therapy, toward a microbiome that is not indicative of a bacterial vaginosis issue, or to correct or otherwise improve a state or symptom of the bacterial vaginosis issue). In Block S150, the therapies can be selected from therapies including one or more of: probiotic therapies, phage-based therapies, prebiotic therapies, small molecule-based therapies, cognitive/behavioral therapies, physical rehabilitation therapies, clinical therapies, medication-based therapies, diet-related therapies, and/or any other suitable therapy designed to operate in any other suitable manner in promoting a user's health. In a specific example of a bacteriophage-based therapy, one or more populations (e.g., in terms of colony forming units) of bacteriophages specific to a certain bacteria (or other microorganism) represented in a subject with the bacterial vaginosis issue can be used to down-regulate or otherwise eliminate populations of the certain bacteria. As such, bacteriophage-based therapies can be used to reduce the size(s) of the undesired population(s) of bacteria represented in the subject. Complementarily, bacteriophage-based therapies can be used to increase the relative abundances of bacterial populations not targeted by the bacteriophage(s) used.

For instance, in relation to the variations of bacterial vaginosis issues described herein, therapies (e.g., probiotic therapies, bacteriophage-based therapies, prebiotic therapies, etc.) can be configured to downregulate and/or upregulate microorganism populations or subpopulations (and/or functions thereof) associated with features characteristic of the bacterial vaginosis issue.

In one such variation, the Block S150 can include one or more of the following steps: obtaining a sample from the subject; purifying nucleic acids (e.g., DNA) from the sample; deep sequencing nucleic acids from the sample so as to determine the amount of one or more of the features of Table A; and comparing the resulting amount of each feature to one or more reference amounts of the one or more of the features listed in one or more of Table A as occurs in an average individual having a bacterial vaginosis issue or an individual not having the bacterial vaginosis issue or both. The compilation of features can sometimes be referred to as a "disease signature" for a specific condition related to a bacterial vaginosis issue. The disease signature can act as a characterization model, and may include probability distributions for control population (no bacterial vaginosis issue) or disease populations having the condition or both. The disease signature can include one or more of the features (e.g., bacterial taxa or genetic pathways) listed and can optionally include criteria determined from abundance values of the control and/or disease populations. Example criteria can include cutoff or probability values for amounts of those features associated with average control or disease (e.g., a bacterial vaginosis issue) individuals.

In a specific example of probiotic therapies, as shown in FIG. 5, candidate therapies of the therapy model can perform one or more of: blocking pathogen entry into an epithelial cell by providing a physical barrier (e.g., by way of colonization resistance), inducing formation of a mucous barrier by stimulation of goblet cells, enhance integrity of apical tight junctions between epithelial cells of a subject (e.g., by stimulating up regulation of zona-occludens 1, by preventing tight junction protein redistribution), producing antimicrobial factors, stimulating production of anti-inflammatory cytokines (e.g., by signaling of dendritic cells and induction of regulatory T-cells), triggering an immune response, and performing any other suitable function that adjusts a subject's microbiome away from a state of dysbiosis.

In variations, the therapy model is preferably based upon data from a large population of subjects, which can comprise the population of subjects from which the microbiome-related datasets are derived in Block S110, wherein microbiome composition and/or functional features or states of health, prior exposure to and post exposure to a variety of therapeutic measures, are well characterized. Such data can be used to train and validate the therapy provision model, in identifying therapeutic measures that provide desired outcomes for subjects based upon different microbiome characterizations. In variations, support vector machines, as a supervised machine learning algorithm, can be used to generate the therapy provision model. However, any other suitable machine learning algorithm described above can facilitate generation of the therapy provision model.

While some methods of statistical analyses and machine learning are described in relation to performance of the Blocks above, variations of the method 100, or any one of FIGS. 1A-1F, can additionally or alternatively utilize any other suitable algorithms in performing the characterization process. In variations, the algorithm(s) can be characterized by a learning style including any one or more of: supervised learning (e.g., using logistic regression, using back propagation neural networks), unsupervised learning (e.g., using an Apriori algorithm, using K-means clustering), semi-supervised learning, reinforcement learning (e.g., using a Q-learning algorithm, using temporal difference learning), and any other suitable learning style. Furthermore, the algorithm(s) can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminant analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolutional network method, a stacked autoencoder method, etc.), a dimensionality reduction method (e.g., principal component analysis, partial least squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and any suitable form of algorithm.

Additionally or alternatively, the therapy model can be derived in relation to identification of a "normal" or baseline microbiome composition and/or functional features, as assessed from subjects of a population of subjects who are identified to be in good health. Upon identification of a subset of subjects of the population of subjects who are characterized to be in good health (e.g., characterized as not having an altered microbiome caused by, or indicative of, a bacterial vaginosis issue, e.g., using features of the characterization process), therapies that modulate microbiome compositions and/or functional features toward those of subjects in good health can be generated in Block S150. Block S150 can thus include identification of one or more baseline microbiome compositions and/or functional features (e.g., one baseline microbiome for each of a set of demographics), and potential therapy formulations and therapy regimens that can shift microbiomes of subjects who are in a state of dysbiosis toward one of the identified baseline microbiome compositions and/or functional features. The therapy model can, however, be generated and/or refined in any other suitable manner.

Microorganism compositions associated with probiotic therapies associated with the therapy model preferably include microorganisms that are culturable (e.g., able to be expanded to provide a scalable therapy) and non-lethal (e.g., non-lethal in their desired therapeutic dosages). Furthermore, microorganism compositions can comprise a single type of microorganism that has an acute or moderated effect upon a subject's microbiome. Additionally or alternatively, microorganism compositions can comprise balanced combinations of multiple types of microorganisms that are configured to cooperate with each other in driving a subject's microbiome toward a desired state. For instance, a combination of multiple types of bacteria in a probiotic therapy can comprise a first bacteria type that generates products that are used by a second bacteria type that has a strong effect in positively affecting a subject's microbiome. Additionally or alternatively, a combination of multiple types of bacteria in a probiotic therapy can comprise several bacteria types that produce proteins with the same functions that positively affect a subject's microbiome.

In examples of probiotic therapies, probiotic compositions can comprise components of one or more of the identified taxa of microorganisms (e.g., as described in Table A) provided at dosages of 1 million to 10 billion CPUs, as determined from a therapy model that predicts positive adjustment of a subject's microbiome in response to the therapy. Additionally or alternatively, the therapy can comprise dosages of proteins resulting from functional presence in the microbiome compositions of subjects without the bacterial vaginosis issue. In the examples, a subject can be instructed to ingest capsules comprising the probiotic formulation according to a regimen tailored to one or more of his/her: physiology (e.g., body mass index, weight, height), demographics (e.g., gender, age), severity of dysbiosis, sensitivity to medications, and any other suitable factor.

Furthermore, probiotic compositions of probiotic-based therapies can be naturally or synthetically derived. For instance, in one application, a probiotic composition can be naturally derived from fecal matter or other biological matter (e.g., of one or more subjects having a baseline microbiome composition and/or functional features, as identified using the characterization process and the therapy model). Additionally or alternatively, probiotic compositions can be synthetically derived (e.g., derived using a benchtop method) based upon a baseline microbiome composition and/or functional features, as identified using the characterization process and the therapy model. In one embodiment, the probiotic composition is or is derived from the subject's own fecal matter that has been stored or "banked" from a period during which the subject is in a healthy state for use when the microbiome is imbalanced (e.g., due to a bacterial vaginosis issue).

In variations, microorganism agents that can be used in probiotic therapies can include one or more of: yeast (e.g., *Saccharomyces boulardii*), gram-negative bacteria (e.g., *E. coli Nissle, Akkermansia muciniphila, Prevotella bryantii*, etc.), gram-positive bacteria (e.g., *Bifidobacterium animalis* (including subspecies *lactis*), *Bifidobacterium longum* (including subspecies *infantis*), *Bifidobacterium bifidum, Bifidobacterium pseudolongum, Bifidobacterium thermophilum, Bifidobacterium breve, Lactobacillus rhamnosus, Lactobacillus acidophilus, Lactobacillus casei, Lactobacillus helveticus, Lactobacillus plantarum, Lactobacillus fermentum, Lactobacillus salivarius, Lactobacillus delbrueckii* (including subspecies *bulgaricus*), *Lactobacillus johnsonii, Lactobacillus reuteri, Lactobacillus gasseri, Lactobacillus brevis* (including subspecies *coagulans*). *Bacillus cereus, Bacillus subtilis* (including var. Natto), *Bacillus polyfermenticus, Bacillus clausii, Bacillus licheniformis, Bacillus coagulans, Bacillus pumilus, Faecalibacterium prausnitzii, Streptococcus thermophilus, Brevibacillus brevis, Lactococcus lactis, Leuconostoc mesenteroides, Enterococcus faecium, Enterococcus faecalis, Enterococcus durans, Clostridium butyricum, Sporolactobacillus inulinus, Sporolactobacillus vineae, Pediococcus acidilactici, Pediococcus pentosaceus*, etc.), and any other suitable type of microorganism agent.

Additionally or alternatively, therapies promoted by the therapy model of Block S150 can include one or more of: consumables (e.g., food items, beverage items, nutritional supplements), suggested activities (e.g., exercise regimens, adjustments to alcohol consumption, adjustments to cigarette usage, adjustments to drug usage), topical therapies (e.g., lotions, ointments, antiseptics, etc.), adjustments to hygienic product usage (e.g., use of shampoo products, use of conditioner products, use of soaps, use of makeup products, etc), adjustments to diet (e.g., sugar consumption, fat consumption, salt consumption, acid consumption, etc.), adjustments to sleep behavior, living arrangement adjustments (e.g., adjustments to living with pets, adjustments to living with plants in one's home environment, adjustments to light and temperature in one's home environment, etc.), nutritional supplements (e.g., vitamins, minerals, fiber, fatty acids, amino acids, prebiotics, probiotics, etc.), medications, antibiotics, and any other suitable therapeutic measure. Among the prebiotics suitable for treatment, as either part of any food or as supplement, are included the following components: 1,4-dihydroxy-2-naphthoic acid (DHNA), inulin, trans-Galactooligosaccharides (GOS), Lactulose, Mannan oligosaccharides (MOS), Fructooligosaccharides (FOS). Neoagaro-oligosaccharides (NAOS), Pyrodextrins, Xylo-oligosaccharides (XOS), Isomalto-oligosaccharides (IMOS), Amylose-resistant starch, Soybean oligosaccharides (SBOS), Lactitol. Lactosucrose (LS), Isomaltulose (including Palatinose), Arabinoxylooligosaccharides (AXOS), Raffinose oligosaccharides (RFO), Arabinoxylans (AX), Polyphenols or any other compound capable of changing the microbiota composition with a desirable effect.

Additionally or alternatively, therapies promoted by the therapy model of Block S150 can include one or more of: different forms of therapy having different therapy orientations (e.g., motivational, increase energy level, reduce weight gain, improve diet, psychoeducational, cognitive behavioral, biological, physical, mindfulness-related, relaxation-related, dialectical behavioral, acceptance-related, commitment-related, etc.) configured to address a variety of factors contributing to an adverse states due to a microbiome that is altered by a bacterial vaginosis issue or a microbiome that is caused by or indicative of a bacterial vaginosis issue; weight management interventions (e.g., to prevent adverse weight-related (e.g., weight gain or loss) side effects due to bacterial vaginosis, or a therapy to prevent, mitigate, or reduce the frequency or severity of bacterial vaginosis); physical therapy; rehabilitation measures; and any other suitable therapeutic measure.

The first method 100 can, however, include any other suitable blocks or steps configured to facilitate reception of biological samples from individuals, processing of biological samples from individuals, analyzing data derived from biological samples, and generating models that can be used to provide customized diagnostics and/or therapeutics according to specific microbiome compositions of individuals.

The methods 100, 200 and/or system of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as RAMS, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

The FIGs illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the Figs. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

VI. Examples for Bacterial Vaginosis

Some examples of sequence groups, discriminating levels, coverage percentages, and discriminating criteria are provided in Table A.

Table A shows data for bacterial vaginosis. The data was obtained from 87 subjects in the condition population and 365 subjects in the control population. Table A shows taxonomic groups for Genus, Family, and Order, and shows functional groups for 14 KEGG L2 functional groups, and 50 KEGG L3 functional groups all in the first column of Table A. As mentioned above, the functional groups correspond to one or more genes with the function. Each of the rows containing data corresponds to a different sequence group. For example, *Lactobacillus* corresponds to a sequence group in the Genus level of the taxonomic hierarchy.

Table A shows a single sequence group for the Genus level. A level can have many sequence groups. The number "1578" after "Lactobacillus" is the NCBI taxonomy ID for that taxonomic group. The IDs correspond to those at "www[dot]ncbi [dot]nlm [dot]nih [dot]gov/Taxonomy/Browser/wwwtax [dot]cgi?id=200643." The p-values are determined via either the Kolmogorov-Smirnov test, or the Welch's t-test.

Sequence groups having a p-value less than 0.01 are shown in the second column. Other sequence groups may exist, but likely would not be selected for inclusion into a disease signature. The third column ("# disease subjects detected") shows the number of samples tested that had the condition of a bacterial vaginosis issue and where the sample exhibited bacteria in the sequence group. The fourth column ("# control subjects detected") shows the number of samples tested that did not have the disease (control) and where the sample exhibited bacteria in the sequence group. The coverage percentage of the sequence group can be determined from the values in the third and fourth columns.

The fifth column shows the mean percentage for the abundance for the subjects having the disease and where the sample exhibited bacteria in the sequence group. The sixth column shows the mean percentage for the abundance for the subjects not having the disease and where the sample exhibited bacteria in the sequence group. As one can see, the sequence groups with the largest percentage difference between the two means have the smallest p-value, signifying a greater separation between the two populations.

A set of sequence groups (taxonomic and/or functional) can be selected from Table A for forming a disease signature that can be used to classify a sample regarding a presence or absence of a microbiome indicative of a bacterial vaginosis issue. For example, 6 sequence groups can be selected, as may occur if all 3 taxonomic groups and 3 KEGG L2 functional groups are selected. The sequence groups for the disease signature can be selected to optimize accuracy for discriminating between the two groups and coverage of the population such that a likelihood of being able to provide a classification is higher (e.g., if a sequence group is not present then that sequence group cannot be used to determine the classification). The total coverage can dependent on the individual coverage percentages and based on the overlap in the coverages among the sequence groups, as described above.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method for characterizing a bacterial vaginosis issue in a subject, the method comprising:
receiving a set of aggregate samples from a population of subjects including a first subset of subjects exhibiting the bacterial vaginosis issue and a second subset of subjects that do not exhibit the bacterial vaginosis issue;
processing nucleic acid content of each of the set of aggregate samples with a fragmentation operation, a multiplexed amplification operation using a set of primers configured to amplify at least two of 16S rRNA sequence, an 18S rRNA sequence or an internally transcribed spacer (ITS) sequence, a sequencing analysis operation, and an alignment operation to generate a microbiome composition dataset for the population of subjects;
receiving a supplementary dataset, associated with at least a subset of the population of subjects, wherein the supplementary dataset is informative of characteristics associated with the bacterial vaginosis issue, wherein the supplementary dataset includes data received from sensors associated with the subjects;
generating a characterization model based on the supplementary dataset and features extracted from the microbiome composition dataset, the characterization model including disease probability distributions for the first subset of subjects or the second subset of subjects; and
determining a set of bacteria taxons for modulating microbiome compositions and/or functional features toward a baseline microbiome composition features associated with a third subset of the population of subjects identified to be in good health based upon analysis of a sample from the subject upon processing the sample with the characterization model; and
administering a therapy to the subject, wherein the therapy is selected from the group consisting of: a prebiotic therapy stimulating the growth of at least a subset of the determined set of bacteria taxons, and a probiotic therapy comprising at least a subset of the determined set of bacteria taxons.

2. The method of claim 1, wherein generating the characterization model comprises performing a statistical analysis to assess a set of microbiome composition features having variations across a first subset of the population of subjects exhibiting the bacterial vaginosis issue and a second subset of the population of subjects not exhibiting the bacterial vaginosis issue.

3. The method of claim 2, wherein generating the characterization model comprises:
extracting candidate features associated with a set of functional aspects of microbiome components indicated in the microbiome composition dataset to generate the microbiome functional diversity dataset; and
characterizing the bacterial vaginosis issue in association with a subset of the set of functional aspects, the subset derived from at least one of clusters of orthologous groups of proteins features, genomic functional features, chemical functional features, and systemic functional features.

4. The method of claim 3, wherein generating the characterization model of the bacterial vaginosis issue comprises generating a characterization that is diagnostic of at least one symptom of bacterial vaginosis.

5. The method of claim 4, wherein generating the characterization that is diagnostic of at least one symptom of the bacterial vaginosis issue comprises generating the characterization upon processing the set of aggregate samples and determining presence of features derived from 1) a set of one or more taxa selected from *Lactobacillus* 1578 (genus), Lactobacillaceae 33958 (family), and Lactobacillales 186826 (order), and 2) a set of functions selected from the group consisting of: microbiome functionality listed in a first dataset for Membrane Transport, Neurodegenerative Diseases, Metabolism of Cofactors and Vitamins, Signaling Molecules and Interaction, Metabolism of Other Amino Acids, Metabolism of Terpenoids and Polyketides, Transcription, Enzyme Families, Amino Acid Metabolism, Endocrine System Biosynthesis of Other Secondary Metabolites, Carbohydrate Metabolism, Replication and Repair, and Transport and Catabolism, and microbiome functionality listed in a second dataset for beta-lactam resistance, Starch and sucrose metabolism, Dioxin degradation Phosphotransferase system (PTS), Lysine degradation, Transporters, Xylene degradation, D-Alanine metabolism, Valine, leucine and isoleucine degradation, Energy metabolism, Pentose phosphate pathway Penicillin and cephalosporin biosynthesis, RNA polymerase Nicotinate and nicotinamide metabolism, Photosynthesis, Photosynthesis proteins, Signal transduction mechanisms, RNA transport, Nitrogen metabolism, Glycine, serine and threonine metabolism, Tryptophan metabolism, Folate biosynthesis, Other transporters Glycolysis/Gluconeogenesis, Bacterial secretion system, Pores ion channels, Galactose metabolism, Amino sugar and nucleotide sugar metabolism, Pantothenate and COA biosynthesis, Peptidases, Oxidative phosphorylation Synthesis and degradation of ketone bodies, Chromosome Transcription factors, Histidine metabolism, Protein folding and associated processing, Glyoxylate and dicarboxylate metabolism, Valine, leucine and isoleucine biosynthesis, Porphyrin and chlorophyll metabolism, Benzoate degradation ABC transporters, Bacterial toxins, Membrane and intracellular structural molecules, DNA repair and recombination proteins, Carbohydrate metabolism, Cytoskeleton proteins, Primary immunodeficiency, Butanoate metabolism, Inorganic ion transport and metabolism, Nucleotide metabolism, and Peroxisome in the at least one of the microbiome composition dataset and the microbiome functional diversity dataset for the population of subjects, wherein the characterization further comprises scoring of the set of one or more taxa or the set of functions in the at least one of the microbiome composition dataset and the microbiome functional diversity dataset determined according to a comparison of an abundance value to one or more reference abundance values for known samples.

6. The method of claim 1, wherein generating the characterization comprises performing a statistical analysis with at least one of a Kolmogorov-Smirnov test and a t-test to assess a set of microbiome composition features having varying degrees of abundance in the first subset of subjects exhibiting the bacterial vaginosis issue and the second subset of subjects not exhibiting the bacterial vaginosis issue, wherein generating the characterization further includes clustering using a Bray-Curtis dissimilarity.

* * * * *